US009388323B2

(12) United States Patent
Zong et al.

(10) Patent No.: US 9,388,323 B2
(45) Date of Patent: *Jul. 12, 2016

(54) LATEX BINDERS, AQUEOUS COATINGS AND PAINTS HAVING FREEZE-THAW ABILITY AND METHODS FOR USING SAME

(75) Inventors: Zhengang Zong, Pennington, NJ (US); Yi-Zhong Li, East Brunswick, NJ (US); Jose Ruiz, Burlington, NJ (US)

(73) Assignee: RHODIA OPERATIONS, Paris (FR)

( * ) Notice: Subject to any disclaimer, the term of this patent is extended or adjusted under 35 U.S.C. 154(b) by 375 days.

This patent is subject to a terminal disclaimer.

(21) Appl. No.: 12/321,256

(22) Filed: Jan. 16, 2009

(65) Prior Publication Data

US 2009/0186968 A1    Jul. 23, 2009

Related U.S. Application Data

(60) Provisional application No. 61/022,206, filed on Jan. 18, 2008, provisional application No. 61/022,443, filed on Jan. 21, 2008, provisional application No. 61/199,936, filed on Nov. 21, 2008.

(51) Int. Cl.
| | |
|---|---|
| C08F 12/04 | (2006.01) |
| C08F 16/22 | (2006.01) |
| C08F 20/36 | (2006.01) |
| C09D 133/02 | (2006.01) |
| C07C 43/23 | (2006.01) |
| C08F 2/24 | (2006.01) |
| C09D 133/08 | (2006.01) |
| C08K 5/00 | (2006.01) |

(52) U.S. Cl.
CPC .............. *C09D 133/02* (2013.01); *C07C 43/23* (2013.01); *C08F 2/24* (2013.01); *C09D 133/08* (2013.01); *C08K 5/0008* (2013.01); *Y10T 428/2982* (2015.01)

(58) Field of Classification Search
CPC .... C09D 125/00; C09D 133/04; C07C 43/02; C07C 43/20; C07C 43/243; C07C 43/245; C08K 5/0008; C08K 5/06
USPC .......................................... 524/543, 558, 560
See application file for complete search history.

(56) References Cited

U.S. PATENT DOCUMENTS

| | | | |
|---|---|---|---|
| 3,965,152 A | 6/1976 | Smith et al. | |
| 4,569,965 A * | 2/1986 | Engel et al. | 524/544 |
| 4,600,516 A | 7/1986 | Wester et al. | 252/8.55 |
| 4,647,610 A | 3/1987 | Sperry et al. | 524/377 |
| 5,082,591 A | 1/1992 | Marchetto et al. | 252/351 |
| 5,211,747 A | 5/1993 | Breton et al. | 106/20 |
| 5,221,496 A | 6/1993 | Holland | 252/143 |
| 5,270,380 A | 12/1993 | Adamson et al. | 524/556 |
| 5,340,394 A | 8/1994 | Elsamanoudi | 106/500 |
| 5,364,904 A | 11/1994 | Farmer et al. | 524/832 |
| 5,399,617 A | 3/1995 | Farwaha et al. | 524/815 |
| 5,610,215 A | 3/1997 | Nonweiler et al. | 524/376 |
| 5,610,225 A | 3/1997 | Farwaha et al. | 524/558 |
| 5,710,347 A | 1/1998 | Nishibori et al. | |
| 5,719,244 A | 2/1998 | Farwaha et al. | 526/238.2 |
| 5,770,760 A * | 6/1998 | Robinson | 560/221 |
| 5,874,495 A | 2/1999 | Robinson | 524/300 |
| 5,874,498 A | 2/1999 | Daniels et al. | 524/563 |
| 5,906,962 A | 5/1999 | Pallas et al. | 504/116 |
| 5,939,514 A | 8/1999 | Brown et al. | 528/229 |
| 6,017,869 A | 1/2000 | Lu et al. | 510/384 |
| 6,022,841 A | 2/2000 | Lu et al. | 510/384 |
| 6,143,710 A | 11/2000 | Lu et al. | 510/384 |
| 6,146,570 A | 11/2000 | Stern | 264/141 |
| 6,204,358 B1 | 3/2001 | Tanaka et al. | |
| 6,218,455 B1 | 4/2001 | Smith et al. | 524/457 |
| 6,258,888 B1 | 7/2001 | Peters et al. | |
| 6,268,327 B1 | 7/2001 | Lu et al. | 510/384 |
| 6,391,952 B1 | 5/2002 | Bett et al. | 524/160 |

(Continued)

FOREIGN PATENT DOCUMENTS

| | | | |
|---|---|---|---|
| EP | 444791 A1 * | 9/1991 | |
| EP | 349383 | 4/1993 | |

(Continued)

OTHER PUBLICATIONS

Bosen, S.F., Bowles, W.A. ,and Person, B.D.; "Antifreezes" Ullmann's Encyclopedia of Industrial Chemistry, 5th Ed., vol. A3, VCR Verlag, pp. 23-32, 1985.
Sarac, A.S., "Redox polymerization", Progress in Polymer Science, vol. 24, No. 8, Oct. 1, 1999, pp. 1149-1204.
Blackley, D.C., Polymer Latices—Science and Technology 2nd Ed., vol. 1, Chapman & Hall, 1997, "Agglomeration by subjecting the latex to freezing and thawing", pp. 278-289.
Aslamazova, T.R., "Stability of Emulsifier-Free Acrylate Latexes with Respect to Freezing and Thawing", Colloid Journal, vol. 61, No. 3, 1999, pp. 268-273.
Andrews, M.D., Journal of Paint Technology 1974, vol. 46, No. 598, pp. 40-46, "Influence of Ethylene and Propylene Glycols on Drying Characteristics of Latex Paints".

(Continued)

*Primary Examiner* — Karuna P Reddy

(57) ABSTRACT

Disclosed are latex polymers and an aqueous coating compositions having excellent freeze-thaw stability, open time, stain resistance, low temperature film formation, foam resistance, block resistance, adhesion, water sensitivity and a low-VOC content. The latex polymers and aqueous coating compositions include at least one latex polymer derived from at least one monomer copolymerized or blended with an alkoxylated compound, for example an alkoxylated tristyrylphenol or an alkoxylated tributylphenol. Also provided is an aqueous coating composition including at least one latex polymer, at least one pigment, water and at least one freeze-thaw additive. Typically, the freeze-thaw additive in an amount greater than about 1.3% by weight of the polymer, typically in an amount greater than about 2% by weight of the polymer, in an amount greater than about 4% by weight of the polymer, in an amount greater than about 7.5% by weight of the polymer, in an amount greater than about 10% by weight of the polymer or in an amount greater than about 20% by weight of the polymer.

18 Claims, 1 Drawing Sheet

(56) References Cited

U.S. PATENT DOCUMENTS

| | | | |
|---|---|---|---|
| 6,410,655 B2 | 6/2002 | Okubo et al. | 525/330.1 |
| 6,465,605 B2 | 10/2002 | Breindel et al. | 528/403 |
| 6,492,445 B2 | 12/2002 | Siddiqui et al. | |
| 6,506,794 B1 | 1/2003 | Sianawati et al. | 514/476 |
| 6,518,354 B1 | 2/2003 | Suzuki et al. | |
| 6,645,605 B2 | 11/2003 | Hammersmith et al. | |
| 6,682,723 B2 | 1/2004 | Parry et al. | 424/62 |
| 6,933,415 B2 | 8/2005 | Zhao et al. | 568/616 |
| 6,946,509 B2 | 9/2005 | He | 524/413 |
| 7,217,758 B2 | 5/2007 | Buckmann et al. | 524/501 |
| 7,238,645 B1 | 7/2007 | Chow et al. | 504/358 |
| 7,488,841 B2 | 2/2009 | Yamawaki et al. | 560/169 |
| 7,659,340 B2 | 2/2010 | Coward et al. | |
| 2002/0077267 A1 | 6/2002 | Parry et al. | 510/337 |
| 2003/0073765 A1 | 4/2003 | Ddamulire et al. | 524/191 |
| 2004/0102568 A1 | 5/2004 | Bridgewater et al. | 524/191 |
| 2004/0209995 A1 | 10/2004 | Adam et al. | 524/800 |
| 2004/0235982 A1 | 11/2004 | Rabasco et al. | 523/191 |
| 2005/0265951 A1 | 12/2005 | Yamawaki et al. | 424/70.22 |
| 2007/0244238 A1 | 10/2007 | Desor et al. | |
| 2008/0058473 A1 | 3/2008 | Freidzon et al. | 525/191 |
| 2008/0119600 A1 | 5/2008 | Anchor et al. | |
| 2009/0076202 A1* | 3/2009 | Seibold et al. | 524/156 |
| 2009/0143502 A1 | 6/2009 | Obie | |
| 2009/0173917 A1 | 7/2009 | Allen et al. | |
| 2009/0186968 A1 | 7/2009 | Zong | |
| 2009/0186972 A1 | 7/2009 | Zong et al. | 524/369 |
| 2010/0016485 A1 | 1/2010 | Zong | |

FOREIGN PATENT DOCUMENTS

| | | | |
|---|---|---|---|
| FR | 2796074 | 1/2001 | B01F 17/00 |
| GB | 2025985 | 1/1980 | |
| JP | 50013485 | 2/1975 | |
| SU | 1068039 | 1/1984 | |
| WO | PCT/IB97/01165 | 9/1997 | A01N 25/14 |
| WO | PCT/US98/06437 | 4/1998 | |
| WO | WO 98/12921 | 4/1998 | A01N 25/14 |
| WO | WO 98/45212 | 10/1998 | C01G 25/02 |
| WO | WO 9919436 | 4/1999 | |
| WO | PCT/US07/008411 | 4/2007 | |
| WO | WO 2007/089807 A2 | 8/2007 | |
| WO | WO 2007/117512 A1 | 10/2007 | C08K 5/06 |
| WO | WO 2009/138523 A2 | 5/2009 | A01N 25/04 |
| WO | WO 2009/138523 A3 | 5/2009 | A01N 25/04 |

OTHER PUBLICATIONS

Akkerman, J., et al., European Coatings Congress, Nuremberg, Germany 2009, Mar. 30-Apr. 1, ID: 10.6, Architectural Coatings, "New developments on open time resins for waterborne decorative coatings".

Overbeek, A., et al., Progress in Organic Coatings 48, 2003, pp. 125-139, "New generation decorative paint technology".

Brunel, L., et al., Nov. 12, 2007, vol. 15, No. 23/Optics Express 15250, "Adaptive Speckle Imaging Interferometry: a new technique for the analysis of micro-structnre dynamics, drying processes and coating formation".

Dihang, Helene, et al., Aug. 2009, Paint & Coatings Industry, pp. 28-31 "Optical Film Formation Analysis".

Crivello, et al., Journal of Polymer Science: Part A Polymer Chemistry, vol. 31, 1847-1857 (1993) "Synthesis and Characterization of Novel Photopolymerizable Multifunctional 2-Propenyl Ether Analogues".

Yoann Lefeuvre, et al., "Optical Film Formation Analysis" presented at The Waterborne Symposium, Advances in Sustainable Coatings Technology, Feb. 18-20, 2009, pp. 91-100.

English Translation of EP 349383.

* cited by examiner

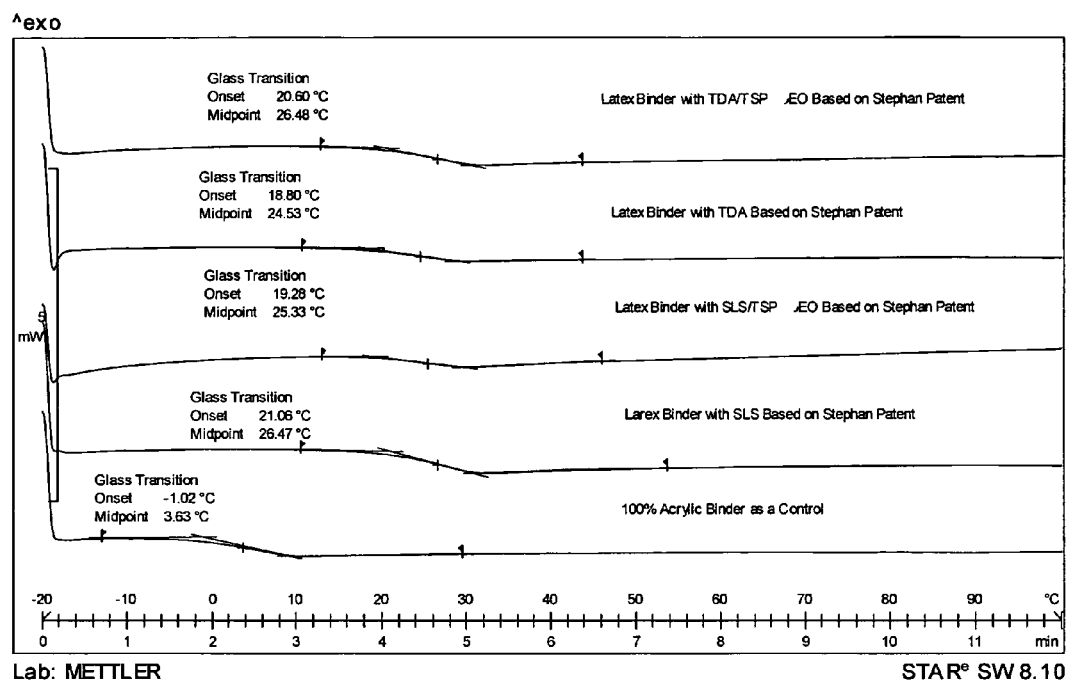

LATEX BINDERS, AQUEOUS COATINGS AND PAINTS HAVING FREEZE-THAW ABILITY AND METHODS FOR USING SAME

CROSS REFERENCE TO RELATED APPLICATIONS

This application claims the benefit of U.S. Provisional Application Ser. No. 61/022,206, filed Jan. 18, 2008, U.S. Provisional Application Ser. No. 61/022,443, filed Jan. 21, 2008 and U.S. Provisional Application Ser. No. 61/199,936, filed Nov. 21, 2008, all herein incorporated by reference

FIELD OF THE INVENTION

The present invention relates to the use of a particular family of alkoxylated compounds, e.g alkoxylated tristyrylphenol and alkoxylated tributylphenol, for improving freeze-thaw stability and open time of aqueous coating compositions such as paint and paper coating compositions. In particular, the present invention relates to the use of certain reactive alkoxylated compound based monomers, surface active alkoxylated compound surfactants, and surface active alkoxylated compound additives for freeze-thaw stability of aqueous latex dispersions, aqueous latex binders and aqueous latex paints.

BACKGROUND OF THE INVENTION

Latex paints are used for a variety of applications including interior and exterior, and flat, semi-gloss and gloss applications. However, paints and aqueous latex dispersions, particularly low VOC paints and latex dispersions, suffer from a lack of freeze-thaw stability. This is particularly a problem during transportation and storage.

Latex freeze-thaw (sometimes herein referred to as "F/T") stability, including the freezing-thawing process, destabilization mechanism, and polymer structures, have been extensively studied since 1950. Blackley, D.C., Polymer Lattices-Science and Technology, $2^{nd}$ Ed., Vol. 1, Chapman & Hall, 1997, gives a comprehensive review of colloidal destabilization of latexes by freezing. The freezing process starts with the decrease of temperature which leads to the formation of ice crystals. The ice crystal structures progressively increase the latex particle concentration in the unfrozen water. Eventually latex particles are forced into contact with each other at the pressure of growing ice crystal structures, resulting in particle aggregation or interparticle coalescence. To make a stable latex dispersion in aqueous medium or latex paints with freeze-thaw stability, various approaches have been employed. The addition of antifreeze agents, e.g. glycol derivatives, has been applied to latex paint to achieve freeze-thaw stability. Thus, latex paints include anti-freeze agents to allow the paints to be used even after they have been subjected to freezing conditions. Exemplary anti-freeze agents include ethylene glycol, diethylene gicol and propylene glycol.

See, Bosen, S. F., Bowles, W. A., Ford, E. A., and Person, B. D., "Antifreezes," Ullmann's Encyclopedia of Industrial Chemistry, $5^{th}$ Ed., Vol. A3, VCH Verlag, pages 23-32, 1985. However, a low or no VOC requirement means the glycol level that can be used has to be reduced or eliminated. Aslamazova, T. R., Colloid Journal, Vol. 61, No. 3, 1999, pp. 268-273, studied the freeze resistance of acrylate latexes and revealed the role of electrostatic contribution to the potential energy of latex particle interactions. Using electrostatic effects on colloidal surface, the interactions of Coulombic repulsion between the charged latex particles lead to higher potential energy. The electrical effects stabilize the latex particles in the freezing and thawing process.

Rajeev Farwaha et. al. (U.S. Pat. No. 5,399,617) discloses the copolymerizable amphoteric surfactants and discloses latex copolymers comprising the copolymerizable amphoteric surfactants impart freeze-thaw stability to the latex paints.

Cheng-Le Zhao et. al. (U.S. Pat. No. 6,933,415 B2) discloses latex polymers including polymerizable alkoxylated surfactants and discloses the low VOC aqueous coatings have excellent freeze-thaw stability.

Rajeev Farwaha et. al. (U.S. Pat. No. 5,610,225) discloses incorporating a monomer with long polyethylene glycol structures to achieve stable freeze-thaw latex.

Masayoshi Okubo et. al. (U.S. Pat. No. 6,410,655 B2) discloses freeze-thaw stability of latex polymers including ethylenic unsaturated monomers.

The additives used as anti-freeze agents are effective for their purposes but are becoming more and more undesirable because they are volatile organic compounds (VOC's). After application of the latex paint to a substrate, the VOC's slowly evaporate into the surroundings.

With strict environmental legislation requiring the reduction of the amount of Volatile Organic Compounds (VOC) in coatings, it is desirable to have paint formulations without or with substantially reduced VOC content, which would include coalescing agents and freeze-thaw agents, among others. Latex binder manufactures are thus forced to develop low VOC binders to meet the requirements of paints and coatings industry. However, low VOC coatings and paints must meet or exceed coating performance standards set in the industry.

In traditional latex binders for architectural coatings, the glass transition temperature is between above 10° C. to about 40° C. However, such architectural coatings often need and contain coalescent agents to soften such latex binders (i.e., soften the latex binders having relatively Tg in the range of above 10° C. to about 40° C.) or anti-freeze agents; both of which are typically high VOC solvents. Thus, these traditional architectural coatings with higher Tg latex binders cannot be formulated to be low VOC without solvents.

For the low VOC application (i.e., low Tg) binders, the average Tg is close to or below 0° C. However, the latex binder with low Tg causes grit when subjected to freeze/thaw cycles as well as exposure to mechanical shear. The resulting coating films are softer and tackier, even after fully dried, and are susceptible to blocking and dirt pick-up effects. Also, such low Tg latex binders and resulting latex paints are not stable, and gel in a cold environmental storage or transportation process. Freeze-Thaw stability of low Tg latex binders and low VOC paints is critically important for transportation, storage, and practical applications. Thus, there is a need to develop latex paints and latex particle dispersions using emulsion polymer technology which meet zero or low VOC requirement and at the same provide excellent mechanical and film performance without sacrificing the freeze-thaw stability of those paints.

SUMMARY OF THE INVENTION

The present invention relates to the use of a particular family of alkoxylated compounds with bulky hydrophobic groups, e.g., alkoxylated tristyrylphenols or alkoxylated tributylphenols, for improving freeze-thaw stability, as well as other properties such as open time, low temperature film formation, stain resistance, film gloss, dispersibility, hiding and scrub resistance, foam resistance, block resistance, adhesion and water sensitivity, among others, of latex binders, paints and coatings. During the thawing process of the freeze-thaw process in latex dispersions and paint formulation, it is believed that the latex particles with high Tg are easy to recover, while the particles with relatively low Tg can not recover from the aggregation or coalescence states which gel.

While not being bound to theory, it is theorized the present invention in part stabilizes the latex particles using steric effects of larger hydrophobic groups to form a protective layer on the surfaces of soft latex particles. The large hydrophobic groups adsorbed or grafted onto the latex particles or co-polymerized into the latex particles prevent these latex particles from approaching the surfaces of other soft latex particles and increase the distance of separation between soft latex particles. The alkylene, e.g., ethylene oxide units from the surfactant of the alkoxylated compounds chains also form a layer which interacts with aqueous medium.

In accordance with the invention, aqueous coating compositions (e.g. latex paints, latex dispersion) including an alkoxylated compound can be produced having excellent freeze-thaw stabilities with the addition of little or no other anti-freeze agents such as glycol, coalescents and high VOC components, more typically with no anti-freeze agents. Freeze-thaw stability or being freeze-thaw stable generally is understood to mean that the composition/formulation does not gel in 3 or more F/T cycles, typically 5 or more F/T cycles.

The alkoxylated compounds can be employed in a number of ways for improving freeze-thaw stability of latex binders, paints and coatings. The present invention may employ polymerizable reactive alkoxylated monomers as a reactant during emulsion polymerization to form the latex polymer. The present invention may employ one or more surface active alkoxylated compounds described herein as a surfactant (emulsifier) during emulsion polymerization to form the latex polymer. The present invention may employ a surface active alkoxylated compound as an additive to a latex polymer-containing aqueous dispersion or concentrate.

In one aspect, the present invention is a latex polymer derived from at least one first monomer and at least one polymerizable reactive alkoxylated second monomer having the structural formula IA:

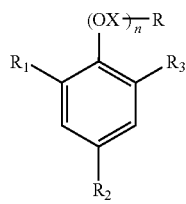

IA wherein R1, R2 and R3 are independently selected from:
—H, tert-butyl, butyl, isobutyl,

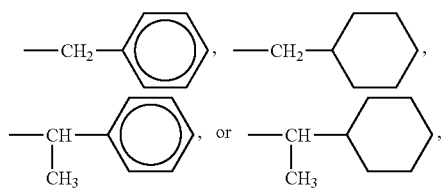

wherein X is a divalent hydrocarbon radical selected from linear or branched alkylene radicals having from 2 to 8 carbon atoms; wherein n is an integer of from 1 to 100, wherein R comprises an ethylenically unsaturated group.

In one embodiment, R can be acrylate, $C_1$-$C_6$ alkyl acrylate, allyl, vinyl, maleate, itaconate or fumarate. R can also be selected from acrylo, methacrylo, acrylamido, methacrylamido, diallylamino, allyl ether, vinyl ether, α-alkenyl, maleimido, styrenyl, and/or α-alkyl styrenyl groups.

In another embodiment, R has a chemical structure: $R^aCH=C(R^b)COO-$, wherein if $R^a$ is H, then $R^b$ is H, $C_1$-$C_4$ alkyl, or —$CH_2COOX$; if $R^a$ is —C(O)OX, then $R^b$ is H or —$CH_2C(O)OX^a$; or if $R^a$ is $CH_3$, then $R^b$ is H and $X^a$ is H or $C_1$-$C_4$ alkyl. R can, in another embodiment, have chemical structure: —HC=CYZ or —OCH=CYZ, wherein Y is H, $CH_3$, or Cl; Z is CN, Cl, —$COOR^c$, —$C_6H_4R^c$, —$COOR^d$, or —HC=$CH_2$; $R^d$ is $C_1$-$C_8$ alkyl or $C_2$-$C_8$ hydroxy alkyl; $R^c$ is H, Cl, Br, or $C_1$-$C_4$ alkyl.

In another aspect, the present invention is a latex polymer derived from at least one first monomer and at least one second monomer having the structural formula IB:

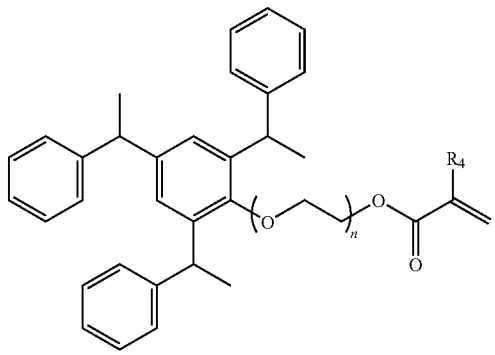

IB wherein n is an integer of from about 1 to about 100, and $R_4$ is selected from H and $C_1$-$C_6$ alkyl. In one embodiment, n is an integer of from about 3 to about 80, typically, about 10 to about 60, and more typically from about 20 to about 50. The at least one first monomer can, in one embodiment, comprise at least one acrylic monomer selected from the group consisting of acrylic acid, acrylic acid esters, methacrylic acid, and methacrylic acid esters. In another embodiment, the latex polymer can be derived from one or more monomers selected from styrene, alpha-methyl styrene, vinyl chloride, acrylonitrile, methacrylonitrile, ureido methacrylate, vinyl acetate, vinyl esters of branched tertiary monocarboxylic acids, itaconic acid, crotonic acid, maleic acid, fumaric acid, ethylene, or $C_4$-$C_8$ conjugated dienes.

In another embodiment, the composition of the present invention is freeze-thaw stable and the polymer has a glass transition temperature (Tg) of between about −15° C. and about 15° C., typically about −15° C. and about 12° C., more typically between about −5° C. and about 5° C., and even more typically between about −5° C. and about 0° C.

In another embodiment, the polymer of the present invention has a mean particle size (sometimes referred to as mean particle diameter, $D_{50}$) of less than about 200 nm, more typically a mean particle size of less than about 190 nm, and most typically a mean particle size of less than about 175 nm.

In a further embodiment, the composition of the present invention is freeze-thaw stable, and the polymer can have a Tg of between about −15° C. and about 12° C. and a mean particle size of less than about 200 nm, or a Tg of between about −5° C. and about 5° C. and a mean particle size of less than about 200 nm, or a Tg of between about −5° C. and about 0° C. and a mean particle size of less than about 200 nm, or a Tg of between about −15° C. and about 12° C. and a mean particle size of less than about 190 nm, or a Tg of between about −5° C. and about 5° C. and a mean particle size of less than about 190 nm, or a Tg of between about −5° C. and about 0° C. and a mean particle size of less than about 190 nm, or a Tg of between about −15° C. and about 12° C. and a mean particle size of less than about 175 nm, or a Tg of between about −5° C. and about 5° C. and a mean particle size of less than about 175 nm, or a Tg of between about −5° C. and about 0° C. and a mean particle size of less than about 175 nm.

In another aspect, the present invention is a latex coating composition comprising: (a) a latex polymer as described above or as described anywhere herein; and (b) water. It is understood that the latex coating composition can contain other additive/ingredients including but not limited to biocides, surfactants, pigments, dispersants, etc. The latex coating composition can further comprise a freeze-thaw additive comprising an ethoxylated tristyrylphenol having the structural formula IC:

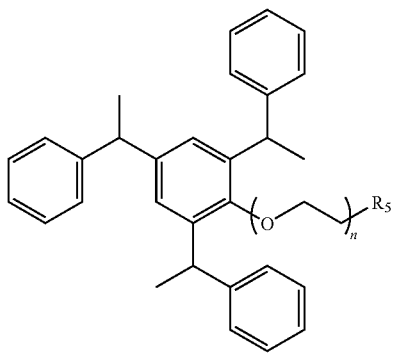

IC wherein, n is an integer of from 1 to 100, wherein $R_5$ is —OH, —OCH$_3$, —OC$_2$H$_5$, —OC$_3$H$_7$, —OC$_4$H$_9$, —OC$_5$H$_{11}$, —OC$_6$H$_{13}$, —Cl, —Br, —CN, Phosphonate (—PO$_3^-$M$^+$), Phosphate (PO$_4^-$M$^+$), Sulfate (SO$_4^-$M$^+$), Sulfonate (SO$_3^-$M$^+$), carboxylate (COO$^-$M$^+$), a nonionic group, or a quaternary ammonium ion, wherein M+ is a cation including but not limited to H$^+$, Na$^+$, NH$_4^+$, K$^+$ or Li$^+$. In one embodiment, n is an integer of from about 1 to 40.

In one embodiment, the latex coating composition contains a freeze-thaw additive in an amount effective to impart freeze-thaw stability to the composition. In one embodiment, the effective amount is greater than about 1.3% by weight of the polymer, typically in an amount greater than about 1.6% by weight of the polymer. In another embodiment, the latex coating composition contains a freeze-thaw additive in an amount greater than about 2% by weight of the polymer, typically in an amount greater than about 4% by weight of the polymer. In another embodiment, the latex coating composition contains a freeze-thaw additive in an amount greater than about 7.5% by weight of the polymer, typically in an amount greater than about 8% by weight of the polymer. In yet another embodiment, the latex coating composition contains a freeze-thaw additive in an amount greater than about 10% by weight of the polymer. In yet another embodiment, the latex coating composition contains a freeze-thaw additive in an amount greater than about 20% by weight of the polymer. In another embodiment, the latex coating composition contains a freeze-thaw additive in an amount between about 1.6% and 7.5% by weight of the polymer.

In one embodiment, the aforementioned latex coating composition is freeze-thaw stable and the latex polymer comprises a glass transition temperature (Tg) of between about −20° C. and about 12° C., typically between about −5° C. and about 5° C., more typically between about −5° C. and about 0° C. In another embodiment, a latex polymer in the aforementioned latex coating has a mean particle size of less than about 200 nm, more typically less than about 190 nm, most typically, less than about 175.

In yet another aspect, the present invention is a method of preparing a latex polymer, comprising copolymerizing (1) at least one first monomer with (2) at least one second monomer, the second monomer a polymerizable reactive tristyrylphenol having the structural formula IA:

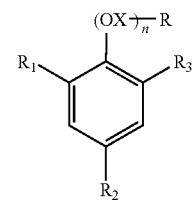

IA wherein R1, R2 and R3 are independently selected from: —H, tert-butyl, butyl, isobutyl,

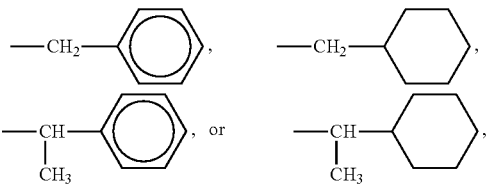

wherein X is a divalent hydrocarbon radical selected from linear or branched alkylene radicals having from 2 to 8 carbon atoms; wherein n is in the range of 1-100, wherein R is an ethylenically unsaturated group including but not limited to acrylate, C$_1$-C$_6$ alkyl acrylate, allyl, vinyl, maleate, itaconate or fumarate. R can also be selected from acrylo, methacrylo, acrylamido, methacrylamido, diallylamino, allyl ether, vinyl ether, α-alkenyl, maleimido, styrenyl, and/or α-alkyl styrenyl groups.

In a further aspect, the present invention is a method of preparing latex polymer, comprising copolymerizing (1) at least one latex monomer with (2) at least one polymerizable reactive tristyrylphenol having the structural formula IB:

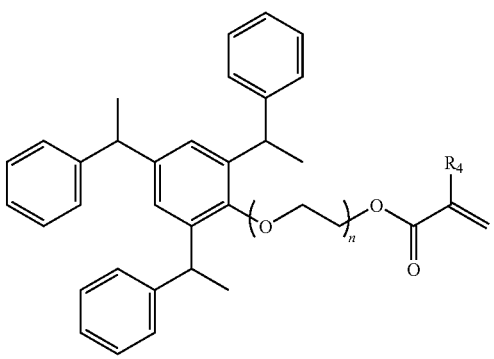

IB wherein n is an integer of from 1 to 100, and $R_4$ is selected from H and $C_1$-$C_{10}$ alkyl, typically $C_1$-$C_6$ alkyl.

In one embodiment, in one or both of the aforementioned methods, an aqueous dispersion of the polymer is freeze-thaw stable, where the polymer comprises a glass transition temperature (Tg) of between about −20° C. and about 20° C., more typically between about −15° C. and about 12° C., most typically between about −5° C. and about 0° C. In another embodiment, the polymer utilized in one or more of the above-referenced methods comprises a mean particle size of less than about 200 nm, more typically a mean particle size of less than about 190 nm, and most typically a mean particle size of less than about 175 nm.

In yet another aspect, the present invention is a method of preparing freeze-thaw stable latex polymer, comprising copolymerizing (1) at least one first monomer with (2) at least one second monomer having the structural formula IB:

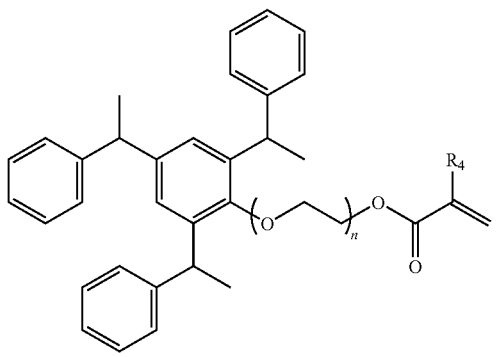

IB wherein n is in the range of 1-100, $R_4$ is selected from the group consisting of H and $C_1$-$C_8$ alkyl, and wherein the polymer has a glass transition temperature (Tg) of between about −15° C. and about 12° C. and a mean particle size of less than about 200 nm, or a Tg of between about −5° C. and about 5° C. and a mean particle size of less than about 200 nm, or a Tg of between about −5° C. and about 0° C. and a mean particle size of less than about 200 nm, or a Tg of between about −15° C. and about 12° C. and a mean particle size of less than about 190 nm, or a Tg of between about −5° C. and about 5° C. and a mean particle size of less than about 190 nm, or a Tg of between about −5° C. and about 0° C. and a mean particle size of less than about 190 nm, or a Tg of between about −15° C. and about 12° C. and a mean particle size of less than about 175 nm, or a Tg of between about −5° C. and about 5° C. and a mean particle size of less than about 175 nm, or a Tg of between about −5° C. and about 0° C. and a mean particle size of less than about 175 nm.

In still a further aspect, the present invention is a low VOC latex coating composition, comprising: (a) at least one latex polymer; (b) at least one pigment; (c) water; and (d) a freeze-thaw additive in an amount greater than about 1.6% by weight of the polymer; wherein the freeze thaw additive comprises an ethoxylated tristyrylphenol having the structural formula IIA:

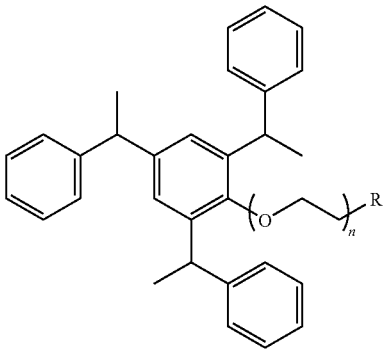

IIA wherein, n is an integer of from 1 to 100, wherein R is —OH, —OCH$_3$, —OC$_2$H$_5$, —OC$_3$H$_7$, —OC$_4$H$_9$, —OC$_5$H$_{11}$, —OC$_6$H$_{13}$, —Cl, —Br, —CN, Phosphonate (—PO$_3^-$M$^+$), Phosphate (PO$_4^-$M$^+$), Sulfate (SO$_4^-$M$^+$), Sulfonate (SO$_3^-$M$^+$), carboxylate (COO$^-$M$^+$), a nonionic group, or a quaternary ammonium ion, wherein M+ is a cation including but not limited to H$^+$, Na$^+$, NH$_4^+$, K$^+$ or Li$^+$. In one embodiment, n is an integer of from about 1 to 40.

In one embodiment, the freeze-thaw additive is present in the latex coating composition in an amount greater than about 2% by weight of the polymer. In another embodiment, the freeze-thaw additive is present in an amount greater than about 4% by weight of the polymer. In yet another embodiment, the freeze-thaw additive is present in an amount greater than about 7.5% by weight of the polymer. In a further embodiment, the freeze-thaw additive is present in an amount greater than about 20% by weight of the polymer. In still a further embodiment, the freeze-thaw additive is present in an amount between about 1.6% and 7.5% by weight of the polymer.

In one embodiment, the at least one latex monomer in the latex coating composition comprises a glass transition temperature (Tg) of between about −15° C. and about 12° C., typically between about −5° C. and about 5° C., more typically between about −5° C. and about 0° C.

In one embodiment, the at least one latex polymer in the latex coating composition comprises has a mean particle size of less than about 200 nm, typically less than about 190 nm, and more typically less than about 175 nm.

In one embodiment, the latex coating composition is characterized by an open time of greater than about 2 minutes, an open time of greater than about 4 minutes, an open time of greater than about 6 minutes or an open time of greater than about 12 minutes.

In a further embodiment, the latex coating composition of the present invention is freeze-thaw stable, wherein the polymer has a Tg of between about −15° C. and about 12° C. and a mean particle size of less than about 200 nm, or a Tg of between about −5° C. and about 5° C. and a mean particle size of less than about 200 nm, or a Tg of between about −5° C. and about 0° C. and a mean particle size of less than about 200 nm, or a Tg of between about −15° C. and about 12° C. and a mean particle size of less than about 190 nm, or a Tg of between about −5° C. and about 5° C. and a mean particle size of less than about 190 nm, or a Tg of between about −5° C. and about 0° C. and a mean particle size of less than about 190 nm, or a Tg of between about −15° C. and about 12° C. and a mean particle size of less than about 175 nm, or a Tg of between about −5° C. and about 5° C. and a mean particle size of less than about 175 nm, or a Tg of between about −5° C. and about 0° C. and a mean particle size of less than about 175 nm, where the latex coating composition is characterized by an open time of greater than about 2 minutes, an open time of greater than about 4 minutes, an open time of greater than about 6 minutes or an open time of greater than about 12 minutes.

In a another embodiment, the latex coating composition of the present invention is freeze-thaw stable where the freeze-thaw additive is present in the latex coating composition in an effective amount, which in one embodiment is greater than about 2% by weight of the polymer, where the polymer has a Tg of between about −15° C. and about 12° C. and a mean particle size of less than about 200 nm, or a Tg of between about −5° C. and about 5° C. and a mean particle size of less than about 200 nm, or a Tg of between about −5° C. and about 0° C. and a mean particle size of less than about 200 nm, or a Tg of between about −15° C. and about 12° C. and a mean particle size of less than about 190 nm, or a Tg of between about −5° C. and about 5° C. and a mean particle size of less than about 190 nm, or a Tg of between about −5° C. and about 0° C. and a mean particle size of less than about 190 nm, or a Tg of between about −15° C. and about 12° C. and a mean particle size of less than about 175 nm, or a Tg of between about −5° C. and about 5° C. and a mean particle size of less than about 175 nm, or a Tg of between about −5° C. and about 0° C. and a mean particle size of less than about 175 nm, where the latex coating composition is characterized by an open time of greater than about 2 minutes, an open time of greater than about 4 minutes, an open time of greater than about 6 minutes or an open time of greater than about 12 minutes.

In a further embodiment, the latex coating composition of the present invention is freeze-thaw stable where the freeze-thaw additive is present in the latex coating composition in an amount greater than about 4% by weight of the polymer, and where the polymer has a Tg of between about −15° C. and about 12° C. and a mean particle size of less than about 200 nm, or a Tg of between about −5° C. and about 5° C. and a mean particle size of less than about 200 nm, or a Tg of between about −5° C. and about 0° C. and a mean particle size of less than about 200 nm, or a Tg of between about −15° C. and about 12° C. and a mean particle size of less than about 190 nm, or a Tg of between about −5° C. and about 5° C. and a mean particle size of less than about 190 nm, or a Tg of between about −5° C. and about 0° C. and a mean particle size of less than about 190 nm, or a Tg of between about −15° C. and about 12° C. and a mean particle size of less than about 175 nm, or a Tg of between about −5° C. and about 5° C. and a mean particle size of less than about 175 nm, or a Tg of between about −5° C. and about 0° C. and a mean particle size of less than about 175 nm, where the latex coating composition is characterized by an open time of greater than about 2 minutes, an open time of greater than about 4 minutes, an open time of greater than about 6 minutes or an open time of greater than about 12 minutes.

In a further embodiment, the latex coating composition of the present invention is freeze-thaw stable where the freeze-thaw additive is present in the latex coating composition in an amount greater than about 7.5% by weight of the polymer, where the polymer has a Tg of between about −15° C. and about 12° C. and a mean particle size of less than about 200 nm, or a Tg of between about −5° C. and about 5° C. and a mean particle size of less than about 200 nm, or a Tg of between about −5° C. and about 0° C. and a mean particle size of less than about 200 nm, or a Tg of between about −15° C. and about 12° C. and a mean particle size of less than about 190 nm, or a Tg of between about −5° C. and about 5° C. and a mean particle size of less than about 190 nm, or a Tg of between about −5° C. and about 0° C. and a mean particle size of less than about 190 nm, or a Tg of between about −15° C. and about 12° C. and a mean particle size of less than about 175 nm, or a Tg of between about −5° C. and about 5° C. and a mean particle size of less than about 175 nm, or a Tg of between about −5° C. and about 0° C. and a mean particle size of less than about 175 nm, where the latex coating composition is characterized by an open time of greater than about 2 minutes, an open time of greater than about 4 minutes, an open time of greater than about 6 minutes or an open time of greater than about 12 minutes.

In a further embodiment, the latex coating composition of the present invention is freeze-thaw stable where the freeze-thaw additive is present in the latex coating composition in an amount greater than about 20% by weight of the polymer, where the polymer has a Tg of between about −15° C. and about 12° C. and a mean particle size of less than about 200 nm, or a Tg of between about −5° C. and about 5° C. and a mean particle size of less than about 200 nm, or a Tg of between about −5° C. and about 0° C. and a mean particle size of less than about 200 nm, or a Tg of between about −15° C. and about 12° C. and a mean particle size of less than about 190 nm, or a Tg of between about −5° C. and about 5° C. and a mean particle size of less than about 190 nm, or a Tg of between about —5° C. and about 0° C. and a mean particle size of less than about 190 nm, or a Tg of between about −15° C. and about 12° C. and a mean particle size of less than about 175 nm, or a Tg of between about −5° C. and about 5° C. and a mean particle size of less than about 175 nm, or a Tg of between about −5° C. and about 0° C. and a mean particle size of less than about 175 nm, where the latex coating composition is characterized by an open time of greater than about 2 minutes, an open time of greater than about 4 minutes, an open time of greater than about 6 minutes or an open time of greater than about 12 minutes.

In a further embodiment, the latex coating composition of the present invention is freeze-thaw stable where the freeze-thaw additive is present in the latex coating composition in an amount between about 1.6% and 7.5% by weight of the polymer, where the polymer has a Tg of between about −15° C. and about 12° C. and a mean particle size of less than about 200 nm, or a Tg of between about −5° C. and about 5° C. and a mean particle size of less than about 200 nm, or a Tg of between about −5° C. and about 0° C. and a mean particle size of less than about 200 nm, or a Tg of between about −15° C. and about 12° C. and a mean particle size of less than about 190 nm, or a Tg of between about −5° C. and about 5° C. and a mean particle size of less than about 190 nm, or a Tg of between about −5° C. and about 0° C. and a mean particle size of less than about 190 nm, or a Tg of between about −15° C. and about 12° C. and a mean particle size of less than about 175 nm, or a Tg of between about −5° C. and about 5° C. and a mean particle size of less than about 175 nm, or a Tg of between about −5° C. and about 0° C. and a mean particle size of less than about 175 nm, where the latex coating composition is characterized by an open time of greater than about 2 minutes, an open time of greater than about 4 minutes, an open time of greater than about 6 minutes or an open time of greater than about 12 minutes.

In still yet another aspect, the present invention is a latex coating composition, comprising: (a) at least one latex polymer; (b) at least one pigment; (c) water; and (d) a freeze-thaw additive in an amount greater than about 1.6% by weight of the polymer; wherein the freeze thaw additive comprises an ethoxylated tributylphenol having the structural formula IIB:

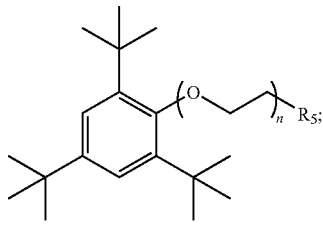

wherein, n is an integer of from 1 to 100, wherein $R_5$ is —OH, —OCH$_3$, —OC$_2$H$_5$, —OC$_3$H$_7$, —OC$_4$H$_9$, —OC$_5$H$_{11}$, —OC$_6$H$_{13}$, —Cl, —Br, —CN, Phosphonate (—PO$_3^-$M$^+$), Phosphate (PO$_4^-$M$^+$), Sulfate (SO$_4^-$M$^+$), Sulfonate (SO$_3^-$M$^+$), carboxylate (COO$^-$M$^+$), a nonionic group, or a quaternary ammonium ion, wherein M+ is a cation including but not limited to H$^+$, Na$^+$, NH$_4^+$, K$^+$ or Li$^+$. In one embodiment, n is an integer of from about 1 to 40.

In one embodiment, the freeze-thaw additive is present in the latex coating composition in an amount greater than about 2% by weight of the polymer. In another embodiment, the freeze-thaw additive is present in an amount greater than about 4% by weight of the polymer. In yet another embodiment, the freeze-thaw additive is present in an amount greater than about 7.5% by weight of the polymer. In a further embodiment, the freeze-thaw additive is present in an amount greater than about 20% by weight of the polymer. In still a further embodiment, the freeze-thaw additive is present in an amount between about 1.6% and 7.5% by weight of the polymer.

In one embodiment, the at least one latex monomer in the latex coating composition comprises a glass transition temperature (Tg) of between about −15° C. and about 12° C., typically between about −5° C. and about 5° C., more typically between about −5° C. and about 0° C.

In one embodiment, the at least one latex monomer in the latex coating composition comprises has a mean particle size of less than about 200 nm, typically less than about 190 nm, and more typically less than about 175 nm.

In one embodiment, the latex coating composition is characterized by an open time of greater than about 2 minutes, an open time of greater than about 4 minutes, an open time of greater than about 6 minutes or an open time of greater than about 12 minutes.

In a further embodiment, the latex coating composition of the present invention is freeze-thaw stable, wherein the polymer has a Tg of between about −15° C. and about 12° C. and a mean particle size of less than about 200 nm, or a Tg of between about −5° C. and about 5° C. and a mean particle size of less than about 200 nm, or a Tg of between about −5° C. and about 0° C. and a mean particle size of less than about 200 nm, or a Tg of between about −15° C. and about 12° C. and a mean particle size of less than about 190 nm, or a Tg of between about −5° C. and about 5° C. and a mean particle size of less than about 190 nm, or a Tg of between about −5° C. and about 0° C. and a mean particle size of less than about 190 nm, or a Tg of between about −15° C. and about 12° C. and a mean particle size of less than about 175 nm, or a Tg of between about −5° C. and about 5° C. and a mean particle size of less than about 175 nm, or a Tg of between about −5° C. and about 0° C. and a mean particle size of less than about 175 nm, where the latex coating composition is characterized by an open time of greater than about 2 minutes, an open time of greater than about 4 minutes, an open time of greater than about 6 minutes or an open time of greater than about 12 minutes.

In a another embodiment, the latex coating composition of the present invention is freeze-thaw stable where the freeze-thaw additive is present in the latex coating composition in an amount greater than about 2% by weight of the polymer, where the polymer has a Tg of between about −15° C. and about 12° C. and a mean particle size of less than about 200 nm, or a Tg of between about −5° C. and about 5° C. and a mean particle size of less than about 200 nm, or a Tg of between about −5° C. and about 0° C. and a mean particle size of less than about 200 nm, or a Tg of between about −15° C. and about 12° C. and a mean particle size of less than about 190 nm, or a Tg of between about −5° C. and about 5° C. and a mean particle size of less than about 190 nm, or a Tg of between about −5° C. and about 0° C. and a mean particle size of less than about 190 nm, or a Tg of between about −15° C. and about 12° C. and a mean particle size of less than about 175 nm, or a Tg of between about −5° C. and about 5° C. and a mean particle size of less than about 175 nm, or a Tg of between about −5° C. and about 0° C. and a mean particle size of less than about 175 nm, where the latex coating composition is characterized by an open time of greater than about 2 minutes, an open time of greater than about 4 minutes, an open time of greater than about 6 minutes or an open time of greater than about 12 minutes.

In a further embodiment, the latex coating composition of the present invention is freeze-thaw stable where the freeze-thaw additive is present in the latex coating composition in an amount greater than about 4% by weight of the polymer, and where the polymer has a Tg of between about −15° C. and about 12° C. and a mean particle size of less than about 200 nm, or a Tg of between about −5° C. and about 5° C. and a mean particle size of less than about 200 nm, or a Tg of between about −5° C. and about 0° C. and a mean particle size of less than about 200 nm, or a Tg of between about −15° C. and about 12° C. and a mean particle size of less than about 190 nm, or a Tg of between about −5° C. and about 5° C. and a mean particle size of less than about 190 nm, or a Tg of between about −5° C. and about 0° C. and a mean particle size of less than about 190 nm, or a Tg of between about −15° C. and about 12° C. and a mean particle size of less than about 175 nm, or a Tg of between about −5° C. and about 5° C. and a mean particle size of less than about 175 nm, or a Tg of between about −5° C. and about 0° C. and a mean particle size of less than about 175 nm, where the latex coating composition is characterized by an open time of greater than about 2 minutes, an open time of greater than about 4 minutes, an open time of greater than about 6 minutes or an open time of greater than about 12 minutes.

In a further embodiment, the latex coating composition of the present invention is freeze-thaw stable where the freeze-thaw additive is present in the latex coating composition in an amount greater than about 7.5% by weight of the polymer, where the polymer has a Tg of between about −15° C. and about 12° C. and a mean particle size of less than about 200 nm, or a Tg of between about −5° C. and about 5° C. and a mean particle size of less than about 200 nm, or a Tg of between about −5° C. and about 0° C. and a mean particle size of less than about 200 nm, or a Tg of between about −15° C. and about 12° C. and a mean particle size of less than about 190 nm, or a Tg of between about −5° C. and about 5° C. and a mean particle size of less than about 190 nm, or a Tg of between about −5° C. and about 0° C. and a mean particle size of less than about 190 nm, or a Tg of between about −15° C. and about 12° C. and a mean particle size of less than about 175 nm, or a Tg of between about −5° C. and about 5° C. and a mean particle size of less than about 175 nm, or a Tg of between about −5° C. and about 0° C. and a mean particle size of less than about 175 nm, where the latex coating composition is characterized by an open time of greater than about 2 minutes, an open time of greater than about 4 minutes, an open time of greater than about 6 minutes or an open time of greater than about 12 minutes.

In a further embodiment, the latex coating composition of the present invention is freeze-thaw stable where the freeze-thaw additive is present in the latex coating composition in an amount greater than about 20% by weight of the polymer, where the polymer has a Tg of between about −15° C. and about 12° C. and a mean particle size of less than about 200 nm, or a Tg of between about −5° C. and about 5° C. and a mean particle size of less than about 200 nm, or a Tg of between about −5° C. and about 0° C. and a mean particle size of less than about 200 nm, or a Tg of between about −15° C. and about 12° C. and a mean particle size of less than about 190 nm, or a Tg of between about −5° C. and about 5° C. and a mean particle size of less than about 190 nm, or a Tg of between about −5° C. and about 0° C. and a mean particle size of less than about 190 nm, or a Tg of between about −15° C. and about 12° C. and a mean particle size of less than about 175 nm, or a Tg of between about −5° C. and about 5° C. and a mean particle size of less than about 175 nm, or a Tg of between about −5° C. and about 0° C. and a mean particle size of less than about 175 nm, where the latex coating composition is characterized by an open time of greater than about 2 minutes, an open time of greater than about 4 minutes, an open time of greater than about 6 minutes or an open time of greater than about 12 minutes.

In a further embodiment, the latex coating composition of the present invention is freeze-thaw stable where the freeze-thaw additive is present in the latex coating composition in an amount between about 1.3% and 7.5% by weight of the polymer, where the polymer has a Tg of between about −15° C. and about 12° C. and a mean particle size of less than about 200 nm, or a Tg of between about −5° C. and about 5° C. and a mean particle size of less than about 200 nm, or a Tg of between about −5° C. and about 0° C. and a mean particle size of less than about 200 nm, or a Tg of between about −15° C. and about 12° C. and a mean particle size of less than about 190 nm, or a Tg of between about −5° C. and about 5° C. and a mean particle size of less than about 190 nm, or a Tg of between about −5° C. and about 0° C. and a mean particle size of less than about 190 nm, or a Tg of between about −15° C. and about 12° C. and a mean particle size of less than about 175 nm, or a Tg of between about −5° C. and about 5° C. and a mean particle size of less than about 175 nm, or a Tg of between about −5° C. and about 0° C. and a mean particle size of less than about 175 nm, where the latex coating composition is characterized by an open time of greater than about 2 minutes, an open time of greater than about 4 minutes, an open time of greater than about 6 minutes or an open time of greater than about 12 minutes.

These and other features and advantages of the present invention will become more readily apparent to those skilled in the art upon consideration of the following detailed description, which describe both the preferred and alternative embodiments of the present invention.

BRIEF DESCRIPTION OF DRAWINGS

FIG. 1 is a chart illustrating the Glass Transition temperature (Tg) of latex binders (prepared from the '514 application description) using different emulsifying surfactants during emulsion polymerization.

DETAILED DESCRIPTION OF THE PREFERRED EMBODIMENTS

The present invention relates to the use of a particular family of alkoxylated compounds, e.g., alkoxylated tristyrylphenols and alkoxylated tributylphenols, provided with an ethylene oxide chain for improving freeze-thaw stability of latex binders and paints. This family of alkoxylated compounds can improve other properties as well, for example, open time, stain resistance, film gloss, dispersibility, hiding and scrub resistance, low temperature film formation, foam resistance, block resistance, adhesion and water sensitivity, among others.

As used herein, the term "alkyl" means a saturated hydrocarbon radical, which may be straight, branched or cyclic, such as, for example, methyl, ethyl, n-propyl, iso-propyl, n-butyl, sec-butyl, t-butyl, pentyl, n-hexyl, cyclohexyl.

As used herein, the term "cycloalkyl" means a saturated hydrocarbon radical that includes one or more cyclic alkyl rings, such as, for example, cyclopentyl, cyclooctyl, and adamantanyl.

As used herein, the term "hydroxyalkyl" means an alkyl radical, more typically an alkyl radical, that is substituted with a hydroxyl groups, such as for example, hydroxymethyl, hydroxyethyl, hydroxypropyl, and hydroxydecyl.

As used herein, the term "alkylene" means a bivalent acyclic saturated hydrocarbon radical, including but not limited to methylene, polymethylene, and alkyl substituted polymethylene radicals, such as, for example, dimethylene, tetramethylene, and 2-methyltrimethylene.

As used herein, the term "alkenyl" means an unsaturated straight chain, branched chain, or cyclic hydrocarbon radical that contains one or more carbon-carbon double bonds, such as, for example, ethenyl, 1-propenyl, 2-propenyl.

As used herein, the term "aryl" means a monovalent unsaturated hydrocarbon radical containing one or more six-membered carbon rings in which the unsaturation may be represented by three conjugated double bonds, which may be substituted one or more of carbons of the ring with hydroxy, alkyl, alkenyl, halo, haloalkyl, or amino, such as, for example, phenoxy, phenyl, methylphenyl, dimethylphenyl, trimethylphenyl, chlorophenyl, trichloromethylphenyl, aminophenyl.

As used herein, the term "aralkyl" means an alkyl group substituted with one or more aryl groups, such as, for example, phenylmethyl, phenylethyl, triphenylmethyl.

As used herein, the terminology "($C_n$-$C_m$)" in reference to an organic group, wherein n and m are each integers, indicates that the group may contain from n carbon atoms to m carbon atoms per group.

As used herein, the terminology "ethylenic unsaturation" means a terminal (that is, e.g., α, β) carbon-carbon double bond.

The present invention includes latex polymers and latex dispersions having low-VOC content and excellent freeze-thaw stability and open time properties compared to conventional aqueous coating compositions, as well as methods of use. Such latex polymers can include at least one latex polymer copolymerized or blended with a particular family of alkoxylated compounds. Typically the latex has a Tg of less than 20° C., more typically less than 15° C., still more typically less than 5° C. More typically, the latex has a Tg in the range of from about −15° C. to about 12° C., more typically from about −5° C. to about 5° C., more typically in the range from −5° C. to about 0° C. In one embodiment, the latex polymer of the present invention has a weight average molecular weight of from about 1,000 to 5,000,000, typically 5,000 to 2,000,000. In another embodiment, the latex polymer of the present invention has a weight average molecular weight of from about 10,000 to 250,000.

The present invention provides aqueous compositions, for example, aqueous coating compositions, having low-VOC content and excellent freeze-thaw stability and open time properties comparable to conventional aqueous coating compositions. The aqueous compositions of the invention are aqueous polymer dispersions which include at least one latex polymer copolymerized or blended with a particular family of alkoxylated compounds, e.g., alkoxylated tristyrylphenol. Generally, the latex polymer is present in such aqueous compositions or paints from about 15% to about 40% by weight of the composition for semigloss and from about 5% to up to about 75%, typically about 5% to about 50% by weight of the composition for flat paint. Paints or other aqueous coatings of the present invention typically further include at least one pigment.

The members of the particular family of alkoxylated compounds, e.g., alkoxylated tristyrylphenols and/or tributylphenols, can be employed in a number ouof ways for improving freeze-thaw stability of latex binders and paints. The present invention may employ polymerizable reactive alkoxylated monomers to form a latex comonomer, surface active alkoxylated compounds as a surfactant (emulsifier) to be present during latex polymer formation, and/or surface active alkoxylated compounds as an additive to an aqueous dispersion of latex polymer or copolymer.

Reactive Polymerizable Tristyrylhenol Ethoxylates

In one embodiment, polymerizable reactive alkoxylated (second) monomer of the following formula IA can be copolymerized (with a first monomer) into the backbone of the latex polymer.

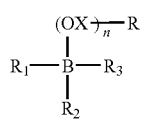

IA wherein B is a 5 or 6 membered cycloalkyl ring, e.g., a cyclohexyl ring, or a single ring aromatic hydrocarbon having a 6 membered ring, e.g., a benzene ring;

R1, R2 and R3 are independently selected from:
—H, butyl, tert-butyl, isobutyl,

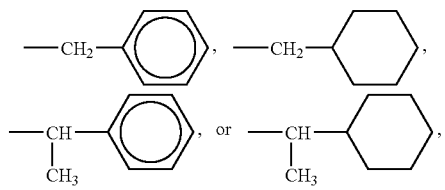

with the proviso that one or none of $R_1$, $R_2$ and $R_3$ is —H.
wherein, X is $C_2H_4$, $C_3H_6$, or $C_4H_8$, or X is a divalent hydrocarbon radical selected from linear or branched alkylene radicals having from 2 to 8 carbon atoms; n is an integer of from 1 to 100, for example from about 4 to 80 or 8 to 25; wherein R is an ethylenically unsaturated group. In one embodiment, n is an integer of from 4 to 80. In one embodiment, n is an integer of from 4 to 60. In one embodiment, n is an integer of from 10 to 50. In one embodiment, n is an integer of from 10 to 25.

Typically, R includes acrylate, or $C_1$-$C_6$ alkyl acrylate, e.g., methacrylate, allyl, vinyl, maleate, itaconate or fumarate, typically R is acrylate or methacrylate.

Suitable polymerizable functional groups R include, for example, acrylo, methacrylo, acrylamido, methacrylamido, diallylamino, allyl ether, vinyl ether, α-alkenyl, maleimido, styrenyl, and α-alkyl styrenyl groups.

For example, suitable polymerizable functional groups R have the chemical structure: $R^aCH{=}C(R^b)COO{-}$, wherein if $R^a$ is H, then $R^b$ is H, $C_1$-$C_4$ alkyl, or —$CH_2COOX$; if $R^a$ is —C(O)OX, then $R^b$ is H or —$CH_2C(O)OX^a$; or if $R^a$ is $CH_3$, then $R^b$ is H and $X^a$ is H or $C_1$-$C_4$ alkyl.

For example, other suitable polymerizable functional groups R have the chemical structure: —HC═CYZ or —OCH═CYZ, wherein Y is H, $CH_3$, or Cl; Z is CN, Cl, —$COOR^c$, —$C_6H_4R^c$, —$COOR^d$, or —HC═$CH_2$; $R^d$ is $C_1$-$C_8$ alkyl or $C_2$-$C_8$ hydroxy alkyl; $R^c$ is H, Cl, Br, or $C_1$-$C_4$ alkyl.

Typically the monomer has the formula IB:

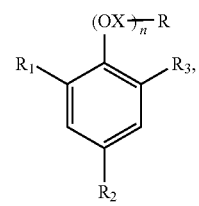

IB wherein, R, $R_1$, $R_2$, $R_3$, X and n are as defined for the structure of formula IA. If desired, the aromatic ring shown in structural formula IB may be saturated. For example, such a saturated monomer may be made by saturating a form of the monomer wherein H is in the R position and then replacing the H in the R position with one of the other above-listed R groups.

In one embodiment, at least one monomer can be copolymerized with a second monomer having structure IB-1:

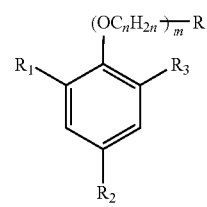

IB-1 wherein R is

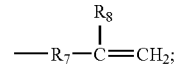

$R_1$, $R_2$ and $R_3$ are each independently H, branched ($C_3$-$C_8$ alkyl), branched ($C_4$-$C_8$)alkene or $R_5$-$R_6$—;

$R_5$ is aryl or ($C_6$-$C_8$)cycloalkyl, $R_6$ is ($C_1$-$C_6$)alkylene, $R_7$ is a divalent linking group, O, ($C_1$-$C_6$)alkylene,

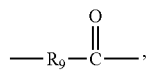

or absent, $R_8$ is H or methyl, $R_9$ is O or $NR_{10}$, $R_{10}$ is H or ($C_1$-$C_4$) alkyl; n is an integer of from 2 to 4, and m is an integer of from 1 to 100.

In one embodiment, $R_1$, $R_2$ and $R_3$ are independently selected from:

—H, butyl, tert-butyl, isobutyl,

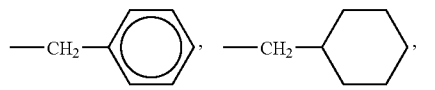

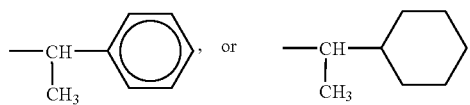

In one embodiment, R can be acrylate, $C_1$-$C_6$ alkyl acrylate, allyl, vinyl, maleate, itaconate or fumarate. In one embodiment, R is at least one of acrylo, methacrylo, acrylamido, methacrylamido, diallylamino, allyl ether, vinyl ether, α-alkenyl, maleimido, styrenyl, and/or α-alkyl styrenyl groups.

In another embodiment, the second monomer is an ethoxylated tributylphenol. In another embodiment, the monomer is an ethoxylated tristyrylphenol. The polymerizable reactive ethoxylated tristyrylphenols have the structural formula IC and the polymerizable reactive ethoxylated tributylphenols have the structural formula IC-1, respectively, as follows:

IC

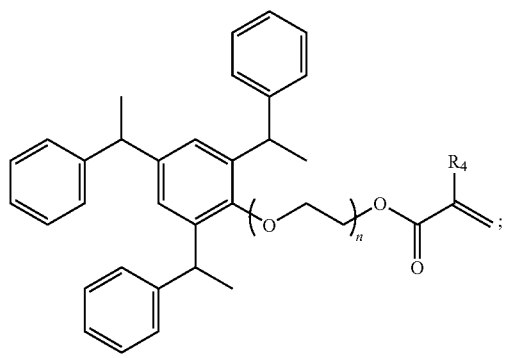

IC-1

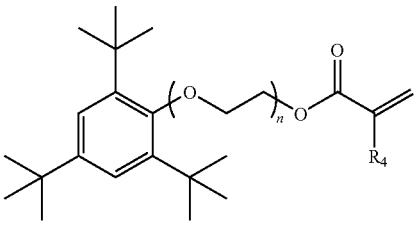

wherein, n is an integer of from 1-100, for example, 4 to 60 or 8 to 25;

$R_4$ is a member of the group H, $C_1$-$C_8$ hydroxy alkyl, $C_1$-$C_6$ alkyl, for example, $CH_3$ or $C_2H_5$.

Thus, the reactive polymerizable ethoxylated tristyrylphenol monomer has a tristyrylphenol portion, an alkylene oxide portion and a reactive substituted or unsubstituted acrylic end group for polymerization. Likewise, the reactive polymerizable ethoxylated tributylphenol monomer has a tributylphenol portion, an alkylene oxide portion and a reactive substituted or unsubstituted acrylic end group for polymerization. If desired, the ethylene oxide group shown in structural formula IC or IC-1 may be replaced with the above discussed —(OX)- group to form an alkoxylated tristyrylphenol or tributylphenol, respectively, and the —C(O)—$CHR_4CH_2$ end group may be replaced by allyl, vinyl, maleate, itaconate or fumarate.

Tristyrylphenol ethoxylates, for other uses, are disclosed by U.S. Pat. No. 6,146,570, published PCT patent application number WO 98/012921 and WO 98/045212, incorporated herein by reference. If desired the aromatic rings of the styryl groups in Formula IC may be saturated.

When reactive polymerizable alkoxylated monomer of IA, IB, IC and/or IC-1 is copolymerized into the backbone of the latex polymer, the latex polymer is made from a mixture wherein the reactive tristyrylphenol or tributylphenol monomer is 1 to 20 parts per 100 parts by weight of monomers used to form the copolymer, more typically 2 to 15, 2 to 8, or 2 to 6 parts per 100 parts by weight of monomers used to form the copolymer. In one embodiment, both the reactive polymerizable alkoxylated monomer of formula IC and IC-1 are utilized and copolymerized into the backbone of a latex polymer.

Other Monomers

In addition to the polymerizable tristyrylphenol monomer and/or polymerizable tributylphenol monomer, there are other monomers from which the at least one latex polymer used in the aqueous coating composition, e.g., paint, is typically derived. For purposes of this description, these other monomers from which latex polymers may be derived are termed latex monomers. Typically, these other latex monomers comprise at least one acrylic monomer selected from the group consisting of acrylic acid, acrylic acid esters, methacrylic acid, and methacrylic acid esters. In addition, the other monomers for making the latex polymer can optionally be selected from one or more monomers selected from the group consisting of styrene, α-methyl styrene, vinyl chloride, acrylonitrile, methacrylonitrile, ureido methacrylate, vinyl acetate, vinyl esters of branched tertiary monocarboxylic acids (e.g. vinyl esters commercially available under the mark VEOVA from Shell Chemical Company or sold as EXXAR Neo Vinyl Esters by ExxonMobil Chemical Company), itaconic acid, crotonic acid, maleic acid, fumaric acid, and ethylene. It is also possible to include $C_4$-$C_8$ conjugated dienes such as 1,3-butadiene, isoprene and chloroprene. Typically, the monomers include one or more monomers selected from the group consisting of n-butyl acrylate, methyl methacrylate, styrene and 2-ethylhexyl acrylate. The latex polymer is typically selected from the group consisting of pure acrylics (comprising acrylic acid, methacrylic acid, an acrylate ester, and/or a methacrylate ester as the main monomers); styrene acrylics (comprising styrene and acrylic acid, methacrylic acid, an acrylate ester, and/or a methacrylate ester as the main monomers); vinyl acrylics (comprising vinyl acetate and acrylic acid, methacrylic acid, an acrylate ester, and/or a methacrylate ester as the main monomers); and acrylated ethylene vinyl acetate copolymers (comprising ethylene, vinyl acetate and acrylic acid, methacrylic acid, an acrylate ester, and/or a methacrylate ester as the main monomers). The monomers can also include other main monomers such as acrylamide and acrylonitrile, and one or more functional monomers such as itaconic acid and ureido methacrylate, as would be readily understood by those skilled in the art. In a particularly preferred embodiment, the latex polymer is a pure acrylic such as a butyl acrylate/methyl methacrylate copolymer derived from monomers including butyl acrylate and methyl methacrylate.

In one embodiment, the reactive polymerizable alkoxylated monomer of formula IA, IB, IC and/or IC-1 are utilized and copolymerized with one of the monomers listed under "other monomers" into the backbone of a latex polymer under reaction conditions. In another embodiment, the reactive polymerizable alkoxylated monomer of formula IA, IB, IC and/or IC-1 are utilized and copolymerized with two or more of the monomers listed under "other monomers" into the backbone of a latex polymer under reaction conditions. In another embodiment, one or more reactive polymerizable alkoxylated monomers of formula IA, IB, IC and/or IC-1 are utilized and copolymerized with one or more of the monomers listed under "other monomers" into the backbone of a latex polymer under reaction conditions.

The latex polymer dispersion typically includes from about 30 to about 75% solids and a mean latex particle size of from about 70 to about 650 nm. In another embodiment, the polymer of the present invention has a mean particle size of less than about 400 nm, typically a mean particle size of less than about 200 nm, more typically a mean particle size of less than about 190 nm, and most typically a mean particle size of less than about 175 nm. In another embodiment, the polymer has a mean particle size of from about 75 nm to about 400 nm.

The latex polymer is typically present in the aqueous coating composition in an amount from about 5 to about 60 percent by weight, and more typically from about 8 to about 40 percent by weight (i.e. the weight percentage of the dry latex polymer based on the total weight of the coating composition).

The resulting aqueous coating composition containing the polymer of the present invention is freeze-thaw stable without having to add anti-freeze agents, or adding small amounts of anti-freeze agents, as described above. Therefore, aqueous coating compositions can be produced in accordance with the invention that possess lower VOC levels than conventional aqueous coating compositions and thus that are more environmentally desirable.

In another embodiment, the resulting latex polymer may be incorporated into an aqueous coating composition along with an emulsion surfactant of the present invention as described below and/or a freeze-thaw additive of the present invention as described below. The addition of the freeze-thaw additive has little or no effect on the VOC levels of the aqueous coating composition, and, thus, aqueous coating compositions can be produced in that possess lower VOC levels than conventional aqueous coating compositions. In such an embodiment, the latex coating composition contains a freeze-thaw additive as described herein in an amount greater than about 1.3% by weight of the polymer. In another embodiment, the latex coating composition contains a freeze-thaw additive as described herein in an amount greater than about 1.6% by weight of the polymer. In another embodiment, the latex coating composition contains a freeze-thaw additive as described herein in an amount greater than about 2% by weight of the polymer. In another embodiment, the latex coating composition contains a freeze-thaw additive as described herein in an amount greater than about 4% by weight of the polymer. In another embodiment, the latex coating composition contains a freeze-thaw additive as described herein in an amount greater than about 7.5% by weight of the polymer. In another embodiment, the latex coating composition contains a freeze-thaw additive as described herein in an amount greater than about 8% by weight of the polymer. In another embodiment, the latex coating composition contains a freeze-thaw additive in an amount between about 1.6% and 7.5% by weight of the polymer. In another embodiment, the latex coating composition contains a freeze-thaw additive in an amount between about 1.6% and 45% by weight of the polymer, typically between about 1.6% and 35% by weight of the polymer.

In a further embodiment, the polymer of the present invention is freeze-thaw stable, and can have a Tg of between about $-15°$ C. and about $12°$ C. and a mean particle size of less than about 200 nm, or a Tg of between about $-5°$ C. and about $5°$ C. and a mean particle size of less than about 200 nm, or a Tg of between about $-5°$ C. and about $0°$ C. and a mean particle size of less than about 200 nm, or a Tg of between about $-15°$ C. and about $12°$ C. and a mean particle size of less than about 190 nm, or a Tg of between about $-5°$ C. and about $5°$ C. and a mean particle size of less than about 190 nm, or a Tg of between about $-5°$ C. and about $0°$ C. and a mean particle size of less than about 190 nm, or a Tg of between about $-15°$ C. and about $12°$ C. and a mean particle size of less than about 175 nm, or a Tg of between about $-5°$ C. and about $5°$ C. and a mean particle size of less than about 175 nm, or a Tg of between about $-5°$ C. and about $0°$ C. and a mean particle size of less than about 175 nm.

The latex polymer including the reactive polymerizable alkoxylated monomer of formula IA, IB or IC can be used in combination with other ionic or non-ionic type of surfactants that are either polymerizable or non-polymerizable, in the aqueous coating composition. In particular, the polymer latex binder can be prepared using emulsion polymerization by feeding the monomers used to form the latex binder to a reactor in the presence of at least one initiator and the at least one reactive polymerizable alkoxylated monomer of formula IA, IB, IC or IC-1 and polymerizing the monomers to produce the latex binder. The monomers fed to a reactor to prepare the polymer latex binder typically include at least one acrylic monomer selected from the group consisting of acrylic acid, acrylic acid esters, methacrylic acid, and methacrylic acid esters. In addition, the monomers can include styrene, vinyl acetate, or ethylene. The monomers can also include one or more monomers selected from the group consisting of styrene, [alpha]-methyl styrene, vinyl chloride, acrylonitrile, methacrylonitrile, ureido methacrylate, vinyl acetate, vinyl esters of branched tertiary monocarboxylic acids, itaconic acid, crotonic acid, maleic acid, fumaric acid, and ethylene. It is also possible to include C4-C8 conjugated dienes such as 1,3-butadiene, isoprene or chloroprene. Typically, the monomers include one or more monomers selected from the group consisting of n-butyl acrylate, methyl methacrylate, styrene and 2-ethylhexyl acrylate. The initiator can be any initiator known in the art for use in emulsion polymerization such as ammonium or potassium persulfate, or a redox system that typically includes an oxidant and a reducing agent. Commonly used redox initiation systems are described e.g., by A. S. Sarac in Progress in Polymer Science 24 (1999), 1149-1204.

The polymer latex binder can be produced by first preparing an initiator solution comprising the initiator and water. A monomer pre-emulsion is also prepared comprising at least a portion of the monomers to be used to form the latex polymer, one or more surfactants (emulsifiers), water, and additional additives such as NaOH. The one or more surfactants in the monomer pre-emulsion include any of the reactive polymerizable alkoxylated monomers of the present invention. The initiator solution and monomer pre-emulsion are then continuously added to the reactor over a predetermined period of time (e.g. 1.5-5 hours) to cause polymerization of the monomers and to thereby produce the latex polymer. Typically, at least a portion of the initiator solution is added to the reactor prior to adding the monomer pre-emulsion. Prior to the addition of the initiator solution and the monomer pre-emulsion, a seed latex such as a polystyrene seed latex can be added to the reactor. In addition, water, one or more surfactants, and any monomers not provided in the monomer pre-emulsion can be added to the reactor prior to adding the initiator and adding the monomer pre-emulsion. The reactor is operated at an elevated temperature at least until all the monomers are fed to produce the polymer latex binder. Once the polymer latex binder is prepared, it is typically chemically stripped thereby decreasing its residual monomer content. Typically, it is chemically stripped by continuously adding an oxidant such as a peroxide (e.g. t-butylhydroperoxide) and a reducing agent (e.g. sodium acetone bisulfite), or another redox pair such as those described by A. S. Sarac in Progress in Polymer Science 24 (1999), 1149-1204, to the latex binder at an elevated temperature and for a predetermined period of time (e.g. 0.5 hours). The pH of the latex binder can then be adjusted and a biocide or other additives added after the chemical stripping step.

The aqueous coating composition is a stable fluid that can be applied to a wide variety of materials such as, for example, paper, wood, concrete, metal, glass, ceramics, plastics, plaster, and roofing substrates such as asphaltic coatings, roofing felts, foamed polyurethane insulation; or to previously painted, primed, undercoated, worn, or weathered substrates. The aqueous coating composition of the invention can be applied to the materials by a variety of techniques well known in the art such as, for example, brush, rollers, mops, air-assisted or airless spray, electrostatic spray, and the like.

Latex Polymer Compositions Comprising Surface Active (Emulsifier) Compound

In another embodiment a surface active compound of structural formula IIA can be used as an emulsifier during the emulsion polymerization reaction used to make latex polymer.

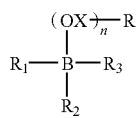

IIA wherein B is a 5 or 6 membered cycloalkyl ring, e.g., a cyclohexyl ring, or a single ring aromatic hydrocarbon having a 6 membered ring, e.g., a benzene ring;

$R_1$, $R_2$ and $R_3$ are independently selected from:
—H, tertbutyl, butyl,

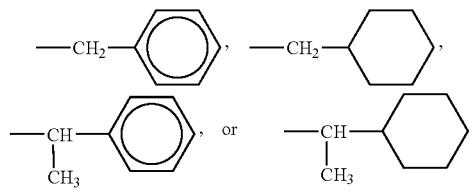

with the proviso that one or none of $R_1$, $R_2$ and $R_3$ is —H.

wherein, X is at least one member of the group consisting of $C_2H_4$, $C_3H_6$, and $C_4H_8$, or wherein X is a divalent hydrocarbon radical selected from linear or branched alkylene radicals having from 2 to 8 carbon atoms; n is 1-100, for example, 3 to 80, 4 to 50, 4 to 40 or 8 to 25;

wherein R is —OH, —OCH$_3$, —OC$_2$H$_5$, —OC$_3$H$_7$, —OC$_4$H$_9$, —OC$_5$H$_{11}$, —OC$_6$H$_{13}$, —Cl, —Br, —CN, Phosphonate (—PO$_3^-$M$^+$), Phosphate (PO$_4^-$M$^+$), Sulfate (SO$_4^-$M$^+$), Sulfonate (SO$_3^-$M$^+$), carboxylate (COO$^-$M$^+$), a non-ionic group, or a quaternary ammonium ion, wherein M+ is a cation including but not limited to H$^+$, Na$^+$, NH$_4^+$, K$^+$ or Li$^+$, In one embodiment, $R_5$ is selected from a quaternary ammonium ion:

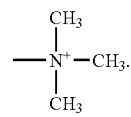

In one embodiment, n is an integer of from 4 to 80. In one embodiment, n is an integer of from 4 to 60. In one embodiment, n is an integer of from 10 to 50. In one embodiment, n is an integer of from 10 to 25.

Typically the alkoxylated surface active compound has the formula IIB:

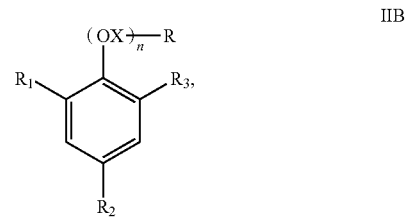

IIB wherein, R, $R_1$, $R_2$, $R_3$, X and n are as defined for the structure of formula IIA. If desired, the aromatic ring shown in structural formula IIB may be saturated.

More typically a surface active alkoxylated tristyrylphenol, e.g., ethoxylated tristyrylphenol, or a surface active alkoxylated tributylphenol, e.g., ethoxylated tributylphenol can be used as an emulsifier during the emulsion polymerization reaction used to make latex polymer. The surface active ethoxylated tristyrylphenols have the structural formula IIC and the surface active ethoxylated tributylphenols have the structural formula IIC-1, respectively, as follows:

IIC

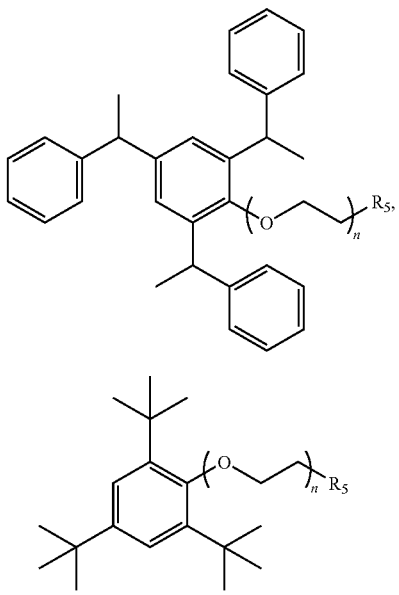

IIC-1 wherein, n is an integer of from 1 to 100 for example, 4 to 60 or 8 to 25, wherein $R_5$ is —OH, —OCH$_3$, —OC$_2$H$_5$, —OC$_3$H$_7$, —OC$_4$H$_9$, —OC$_5$H$_{11}$, —OC$_6$H$_{13}$, —Cl, —Br, —CN, Phosphonate (—PO$_3^-$M$^+$), Phosphate (PO$_4^-$M$^+$), Sulfate (SO$_4^-$M$^+$), Sulfonate (SO$_3^-$M$^+$), carboxylate (COO$^-$M$^+$), a nonionic group, or a quaternary ammonium ion, wherein M+ is a cation including but not limited to H$^+$, Na$^+$, NH$_4^+$, K$^+$ or Li$^+$.

In one embodiment, $R_5$ is selected from a quaternary ammonium ion:

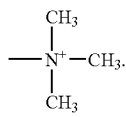

In one embodiment, n is an integer of from 4 to 80. In one embodiment, n is an integer of from 4 to 60. In one embodiment, n is an integer of from 10 to 50. In one embodiment, n is an integer of from 10 to 25.

When surface active ethoxylated tristyrylphenol or ethoxylated tributylphenol is employed as an emulsifier in emulsion polymerization to form the latex polymer, the latex polymer is made from a mixture wherein the surface active emulsifier utilized is. In one embodiment, the emulsifier is added in an amount greater than 1.3% by weight of the polymer or monomers used to form the latex polymer, in an amount greater than 1.6% by weight of the polymer or monomers used to form the latex polymer, typically in an amount greater than about 2% by weight of the polymer or monomers used to form the latex polymer, more typically in an amount greater than about 4% by weight of the polymer or monomers used to form the latex polymer, and most typically in an amount greater than about 7.5% by weight of the polymer or monomers used to form the latex polymer. In another embodiment, the latex coating composition contains an emulsifier in an amount greater than about 8% by weight of the polymer or monomers used to form the latex polymer, or greater than about 10% by weight of the polymer or monomers. In another embodiment, the emulsifier is added is between about 1.6% and 7.5% by weight of the polymer or monomers used to form the latex polymer. In another embodiment, emulsifier added is between about 1.6% and 45% by weight of the polymer or monomers used to form the latex polymer, typically between about 1.6% and 35% by weight of the polymer or monomers used to form the latex polymer If desired the ethylene oxide repeating units of the ethylene oxide chain of formula IIC or IIC-1 may be replace by the above-described —(OX)— group to form alkoxylated tristyrylphenol or alkoxylated tributylphenol.

The typical monomers from which the at least one latex polymer (sometimes referred to herein as first monomer or third monomer) is formed are described above in the section entitled "Other Monomers".

As described above, the polymer latex binder can be produced by first preparing an initiator solution comprising the initiator and water. A monomer pre-emulsion is also prepared comprising at least a portion of the monomers to be used to form the latex polymer, one or more surfactants (emulsifiers), water, and additional additives such as NaOH. The one or more surfactants in the monomer pre-emulsion include the surface active alkoxylated compound of the invention. Thus, the alkoxylated compound is employed as an emulsifier to form a blend rather than as a reactant which copolymerizes with the other monomers which form the polymer latex binder. The initiator solution and monomer pre-emulsion are then continuously added to the reactor over a predetermined period of time (e.g. 1.5-5 hours) to cause polymerization of the monomers and to thereby produce the latex polymer. Typically, at least a portion of the initiator solution is added to the reactor prior to adding the monomer pre-emulsion. Prior to the addition of the initiator solution and the monomer pre-emulsion, a seed latex such as a polystyrene seed latex can be added to the reactor. In addition, water, one or more surfactants, and any monomers not provided in the monomer pre-emulsion can be added to the reactor prior to adding the initiator and adding the monomer pre-emulsion. The reactor is operated at an elevated temperature at least until all the monomers are fed to produce the polymer latex binder. Once the polymer latex binder is prepared, it is typically chemically stripped thereby decreasing its residual monomer content. Typically, it is chemically stripped by continuously adding an oxidant such as a peroxide (e.g. t-butylhydroperoxide) and a reducing agent (e.g. sodium acetone bisulfite), or another redox pair such as those described by A. S. Sarac in Progress in Polymer Science 24 (1999), 1149-1204, to the latex binder at an elevated temperature and for a predetermined period of time (e.g. 0.5 hours). The pH of the latex binder can then be adjusted and a biocide or other additives added after the chemical stripping step.

The incorporation of the surface active alkoxylated compound surfactant (emulsifier) in the emulsion polymerization reaction mixture enables the coating composition to have a lower VOC content while maintaining the freeze-thaw stability of the aqueous coating composition at desirable levels.

Additive to an Aqueous Latex Dispersion

In another embodiment the above-described surface active alkoxylated compound of structural formula IIA, IIB, IIC or IIC-1 (sometimes referred to as the freeze-thaw additive) can be used as an additive to an already formed aqueous dispersion of latex polymer. It is understood, that the freeze-thaw additive can be added any point in the production of the aqueous coating composition, including but not limited to during the emulsification step, during formulation, etc. It is also understood that the freeze-thaw additive can be post-added to the aqueous coating composition or a concentrate thereof.

This results in an aqueous composition comprising the surface active alkoxylated compound and the latex polymer. When the surface active alkoxylated compound is employed as an additive to an already formed aqueous latex dispersion, the resulting composition has alkoxylated compound additive in an amount of about 1 to 10, Typically 2 to 8 or 2 to 6, parts per 100 parts by weight of monomers used to form the latex polymer.

The typical monomers from which the latex polymer is formed are described above in the section entitled "Other Monomers" and can be copolymerized with the reactive monomers of the present invention as described above.

The present invention further includes a method of preparing a latex binder composition, comprising adding the at least one surface active alkoxylated compound surfactant (emulsifier) of structural formula IIA, IIB, IIC and/or IIC-1 as described above to an aqueous dispersion of a latex polymer to produce the latex binder. The at least one pigment and other additives can then be mixed with the resulting latex binder to produce the aqueous coating composition in any appropriate order. The addition of the surface active alkoxylated compound of structural formula IIA, IIB, IIC or IIC-1 to the latex polymer forms a mixture having a lower VOC content while maintaining the freeze-thaw stability of the mixture at desirable levels.

In another embodiment the above-described surface active compound of structural formula IIA, IIB, IIC or IIC-1 (sometimes referred to as the freeze-thaw additive) can be used as an additive to an during formulation of paint or aqueous coating composition. Formulation is the stage at which additives are added to a base aqueous latex polymer dispersion to make it into final product such as a paint or coating. When the surface active alkoxylated compound is employed as an additive to an already formed paint or aqueous coating composition, e.g., aqueous latex coating dispersion, the resulting composition has alkoxylated compound additive typically in an amount greater than about 1.3% by weight of the polymer or monomers used to form the latex polymer, more typically in an amount greater than about 1.6% by weight of the polymer or monomers used to form the latex polymer, yet more typically in an amount greater than about 2% by weight of the polymer or monomers used to form the latex polymer, even more typically in an amount greater than about 4% by weight of the polymer or monomers used to form the latex polymer, and most typically in an amount greater than about 7.5% by weight of the polymer or monomers used to form the latex polymer. In another embodiment, the latex coating composition contains surface active alkoxylated compound in an amount between about 1.6% and 7.5% by weight of the polymer or monomers used to form the latex polymer.

In another embodiment, the latex coating composition contains surface active alkoxylated compound in an amount between about 1.6% and 45% by weight of the polymer or monomers used to form the latex polymer, typically between about 1.6% and 35%. Pigment is a typical additive, for example, added during formulation of paint from raw aqueous latex polymer dispersion.

The aqueous coating compositions of the present invention are freeze-thaw stable where the freeze-thaw additive is present in the aqueous coating composition in the amounts by weight of the polymer as described above, where the polymer can have a Tg of between about −15° C. and about 12° C. and a mean particle size of less than about 200 nm, or a Tg of between about −5° C. and about 5° C. and a mean particle size of less than about 200 nm, or a Tg of between about −5° C. and about 0° C. and a mean particle size of less than about 200 nm, or a Tg of between about −15° C. and about 12° C. and a mean particle size of less than about 190 nm, or a Tg of between about −5° C. and about 5° C. and a mean particle size of less than about 190 nm, or a Tg of between about −5° C. and about 0° C. and a mean particle size of less than about 190 nm, or a Tg of between about −15° C. and about 12° C. and a mean particle size of less than about 175 nm, or a Tg of between about −5° C. and about 5° C. and a mean particle size of less than about 175 nm, or a Tg of between about −5° C. and about 0° C. and a mean particle size of less than about 175 nm. As described above, the mean particle size is typically between about 75 nm to about 400 nm. The aqueous coating composition can be characterized by an open time of greater than about 2 minutes, an open time of greater than about 4 minutes, an open time of greater than about 6 minutes or an open time of greater than about 12 minutes.

The present invention further includes a method of preparing a paint or aqueous coating composition, comprising adding the at least one surface active alkoxylated compound of structural formula IIA, IIB, IIC and/or IIC-1 as described above during formulation of paint or aqueous coating composition comprising at least one pigment and other additives to produce the final paint or aqueous coating composition. The addition of the surface active alkoxylated compound surfactant (emulsifier) during formulation of paint or aqueous coating composition forms a coating composition having a lower VOC content while maintaining the freeze-thaw stability of the aqueous coating composition at desirable levels.

Other Additives

The aqueous coating compositions of the invention include at least one latex polymer derived from at least one monomer, for example acrylic monomers and/or the other above-described latex monomers. The aqueous coating compositions of the invention include less than 2% by weight and typically less than 1.0% by weight of anti-freeze agents based on the total weight of the aqueous coating composition. More typically, the aqueous coating compositions are substantially free of anti-freeze agents.

The aqueous coating composition typically includes at least one pigment. The term "pigment" as used herein includes non-film-forming solids such as pigments, extenders, and fillers. The at least one pigment is typically selected from the group consisting of $TiO_2$ (in both anastase and rutile forms), clay (aluminum silicate), $CaCO_3$ (in both ground and precipitated forms), aluminum oxide, silicon dioxide, magnesium oxide, talc (magnesium silicate), barytes (barium sulfate), zinc oxide, zinc sulfite, sodium oxide, potassium oxide and mixtures thereof. Suitable mixtures include blends of metal oxides such as those sold under the marks MINEX (oxides of silicon, aluminum, sodium and potassium commercially available from Unimin Specialty Minerals), CELITES (aluminum oxide and silicon dioxide commercially available from Celite Company), ATOMITES (commercially available from English China Clay International), and ATTAGELS (commercially available from Engelhard). More typically, the at least one pigment includes $TiO_2$, $CaCO_3$ or clay. Generally, the mean particle sizes of the pigments range from about 0.01 to about 50 microns. For example, the $TiO_2$ particles used in the aqueous coating composition typically have a mean particle size of from about 0.15 to about 0.40 microns. The pigment can be added to the aqueous coating composition as a powder or in slurry form. The pigment is typically present in the aqueous coating composition in an amount from about 5 to about 50 percent by weight, more typically from about 10 to about 40 percent by weight.

The coating composition can optionally contain additives such as one or more film-forming aids or coalescing agents.

Suitable firm-forming aids or coalescing agents include plasticizers and drying retarders such as high boiling point polar solvents. Other conventional coating additives such as, for example, dispersants, additional surfactants (i.e. wetting agents), rheology modifiers, defoamers, thickeners, biocides, mildewcides, colorants such as colored pigments and dyes, waxes, perfumes, co-solvents, and the like, can also be used in accordance with the invention. For example, non-ionic and/or ionic (e.g. anionic or cationic) surfactants can be used to produce the polymer latex. These additives are typically present in the aqueous coating composition in an amount from 0 to about 15% by weight, more typically from about 1 to about 10% by weight based on the total weight of the coating composition.

As mentioned above, the aqueous coating composition in some embodiments can include less than 2.0% of anti-freeze agents based on the total weight of the aqueous coating composition. Exemplary anti-freeze agents include ethylene glycol, diethylene glycol, propylene glycol, glycerol (1,2,3-trihydroxypropane), ethanol, methanol, 1-methoxy-2-propanol, 2-amino-2-methyl-1-propanol, and FTS-365 (a freeze-thaw stabilizer from Inovachem Specialty Chemicals). More typically, the aqueous coating composition includes less than 1.0% or is substantially free (e.g. includes less than 0.1%) of anti-freeze agents. Accordingly, the aqueous coating composition of the invention typically has a VOC level of less than about 100 g/L and more typically less than or equal to about 50 g/L. Despite the fact that the aqueous coating compositions of the invention include little or no anti-freeze agents, the compositions possess freeze-thaw stabilities at levels desirable in the art.

For example, the aqueous coating compositions of the invention can be subjected to freeze-thaw cycles using ASTM method D2243-82 or ASTM D2243-95 without coagulation.

The balance of the aqueous coating composition of the invention is water. Although much of the water is present in the polymer latex dispersion and in other components of the aqueous coating composition, water is generally also added separately to the aqueous coating composition. Typically, the aqueous coating composition includes from about 10% to about 85% by weight and more typically from about 35% to about 80% by weight water. Stated differently, the total solids content of the aqueous coating composition is typically from about 15% to about 90%, more typically, from about 20% to about 65%.

The coating compositions are typically formulated such that the dried coatings comprise at least 10% by volume of dry polymer solids, and additionally 5 to 90% by volume of non-polymeric solids in the form of pigments. The dried coatings can also include additives such as plasticizers, dispersants, surfactants, rheology modifiers, defoamers, thickeners, biocides, mildewcides, colorants, waxes, and the like, that do not evaporate upon drying of the coating composition.

In one preferred embodiment of the invention, the aqueous coating composition is a latex paint composition comprising at least one latex polymer derived from at least one acrylic monomer selected from the group consisting of acrylic acid, acrylic acid esters, methacrylic acid, and methacrylic acid esters and at least one polymerizable alkoxylated surfactant; at least one pigment and water. As mentioned above, the at least one latex polymer can be a pure acrylic, a styrene acrylic, a vinyl acrylic or an acrylated ethylene vinyl acetate copolymer.

The present invention further includes a method of preparing an aqueous coating composition by mixing together at least one latex polymer derived from at least one monomer and copolymerized and/or blended with at least one tristyrylphenol as described above, and at least one pigment. Typically, the latex polymer is in the form of a latex polymer dispersion. The additives discussed above can be added in any suitable order to the latex polymer, the pigment, or combinations thereof, to provide these additives in the aqueous coating composition. In the case of paint formulations, the aqueous coating composition typically has a pH of from 7 to 10.

The present invention will now be further described by the following non-limiting examples. As described above, the present invention may employ (I) surface active alkoxylated compounds as a surfactant (emulsifier) to be present during latex polymer formation, (II) polymerizable reactive alkoxylated monomers to form a latex comonomer, and/or (III) surface active alkoxylated compounds as an additive to an aqueous dispersion of latex polymer or copolymer.

EXAMPLES

The following Example 1 and its subsets describe the present invention as surface active alkoxylated compounds utilized as a surfactant (emulsifier) to be present during latex polymer formation.

Example 1

Freeze Thaw Stability Study—Example 1 compares a control with compositions of the present invention, which incorporate various levels of TSP-EO and 1% MM (methacrylic acid). TSP-EO is a surface active ethoxylated tristyrylphenol according to the above-listed structural formula IIC in which the R group is H.

Sample 1 of the present invention with 2% TSP-EO, 1% MM (methacrylic acid); Sample 2 of the present invention with 4% TSP-EO, 1% MM; and Sample 3 of the present invention with 6% TSP-EO, 1% MM were made. TABLE 1 shows the ingredients of Sample 2 which is an embodiment of the present invention with 4% TSP-EO, 1% MM.

TABLE 1

SAMPLE 2 INGREDIENTS

| Recipe: | Ingredient weight (grams) | % BOTM |
|---|---|---|
| Kettle Charge | | |
| Deionized Water | 200.00 | |
| Monomer Emulsion | | |
| Deionized Water | 176.25 | |
| Alkyl sulfate surfactant | 18.75 | 1.50 |
| Non-ionic surfactant | 5.00 | 0.50 |
| TSP - EO | 20.00 | 4.00 |
| Methylmethacrylate (MMA) | 200.00 | 40.00 |
| butylacrylate (BA) | 295.00 | 59.00 |
| (methyl acrylic acid) MAA | 5.00 | 1.00 |
| Initiator Solution | | |
| Deionized Water | 98.00 | |
| Ammonium Persulfate | 2.00 | 0.40 |
| Total | 1020.00 | 106.40 |
| Total | 1020.00 | |
| Theoretical % Solids = | | |

"BOTM" is an abbreviation for "Based On Total Monomer." The monomer emulsion contains typical monomers for making latex. As mentioned above, TSP-EO contains a surface active tristyrylphenol with from about 10 to about 50 ethylene oxide groups in its alkoylate chain according to the above-listed structural formula IIC in which the R group is H.

RHODACAL A-246/L and ABEX are emulsifiers available from Rhodia Inc., Cranbury, N.J.

TABLE 2 shows the ingredients employed in a control tested in this example.

TABLE 2

CONTROL INGREDIENTS

| Recipe: | Ingredient weight (g) | % BOTM |
|---|---|---|
| Kettle Charge | | |
| Deionized Water | 320.00 | |
| Monomer Emulsion | | |
| Deionized Water | 282.00 | |
| Alkyl sulfate surfactant | 30.00 | 1.50 |
| Non-ionic surfactant | 8.00 | 0.50 |
| Methylmethacrylate (MMA) | 320.00 | 40.00 |
| butylacrylate (BA) | 472.00 | 59.00 |
| (methyl acrylic acid) MAA | 8.00 | 1.00 |
| Initiator Solution | | |
| Deionized Water | 156.80 | |
| Ammonium Persulfate | 3.20 | 0.40 |
| Total | 1600.00 | 102.40 |
| Total Theoretical % Solids = | | |

PROCEDURE: The control and the Sample 1, 2 and 3 ingredients were respectively each employed in an emulsion polymerization reaction procedure as follows:

1. Heat kettle charge to about 80° C. while purging with $N_2$. Maintain $N_2$ blanket throughout run.

2. Prepare Monomer emulsion and Initiator solution based on the above described recipe.

3. At about 80° C. add Initiator solution and Monomer emulsion to the kettle.

4. Hold at about 80° C. for about 10-20 minutes.

5. Slowly add the remainder of the Monomer emulsion and Initiator solution over 3 hours while maintaining the reaction temperature at about 80±1° C.

6. After addition of the Monomer emulsion and Initiator solution is completed, the reaction mixture temperature was heated to about 85° C. and held over 30 minutes.

7. Cool reactor contents to below about 30° C. Adjust the pH of final reaction to 8-9.

8. Filter the batch through a 100 mesh filter and store in a closed container for characterization.

Sample 1 contained 4% TSP-EO. The procedure was repeated for 2% TSP-EO and 6% TSP-EO samples that were the same as the 4% TSP-EO sample except for the amount of TSP-EO.

TABLE 3 shows the results of the control, the 2% TSP-EO sample (Sample 1), the above-described 4% TSP-EO sample (Sample 2), and the 6% TSP-EO sample (Sample 3). The freeze-thaw stability of polymer dispersions and formulated paints was measured based on ASTM standard test Method D2243-95. The latexes or formulated paints are tested using a half pint of sample. The sample was kept in a freezer at 0° F. (−18° C.) over 17 hours and then taken out from the freezer and allowed to thaw for 7 hours at room temperature. The freeze-thaw cycles were continued until the latex or paint coagulated, or to a maximum of five (5) cycles.

TABLE 3

| | Control | 2% TSP - EO (Sample 1) | 4% TSP - EO (Sample 2) | 6% TSP - EO (Sample 3) |
|---|---|---|---|---|
| 1. Coagulum (based on total latex) | 0.5 | 17 | 0.5 | 0.5 |
| 2. pH of aqueous latex dispersion after neutralization | 8.86 | 8.83 | 8.9 | 8.81 |
| 3. Latex Solid in dispersion, % | 50.78 | 49.94 | 51.1 | 51.6 |
| 4. Brookfield Viscosity of aqueous latex polymer dispersion | | | | |
| Spindle/Instrument Used at 60 rpm (cps) | LV3/LVT Model 100 | LV3/ LVT Model 90 | LV3/ LVT Model 70 | LV3/ LVT Model 70 |
| 5. Particle Size | | | | |
| Weight Average | 180.6 | 172.8 | 164.2 | 156.3 |
| Std. Dev. % | 11.73 | 6.73 | 9.8 | 9.9 |
| 6. Freeze-Thaw Stability | | | | |
| Cycle 1 (cps) | gelled | 400 | 600 | 1560 |
| Cycle 2 | | 520 | 680 | 1500 |
| Cycle 3 | | 500 | 580 | 1300 |

TABLE 3 shows the additive of the present invention prevented gelling at conditions which gelled the control. Coagulum particles are formed as a byproduct of making latex. The Tg of the latex, as measured using the DSC method as generally known in the art, was 3.63° C.

Example 1-1

The above-described procedure was repeated with a variety of anionic or nonionic ethoxylated tristerylphenolic (TSP) compounds having from about 6 ethylene oxide groups to about 60 ethylene oxide groups. TABLE 4 presents the results of these examples.

TABLE 4

Effects of Additives on Freeze-Thaw Stability of Water-Borne Paints[2]

| | | Freeze-Thaw Stability Viscosity (KU)[1] | | | | |
|---|---|---|---|---|---|---|
| Additives | Starting Viscosity | 1 cycle | 2 cycles | 3 cycles | 4 cycles | 5 cycles |
| TSP-EO #1 | 102.4 | 103.8 | 104.3 | 104 | 104 | 105.4 |
| TSP-EO #2 | 98.3 | 101.9 | 102.2 | 101.2 | 100.2 | 101.3 |
| TSP-EO #3 | 82.9 | 86.6 | 88.8 | 89.4 | 90.4 | 91.5 |
| TSP-EO #4 | 78 | 88.3 | 90.2 | 91.6 | 93.3 | 101.4 |
| TSP-EO #5 | 78.4 | 82 | 86.4 | 86 | 85.4 | 87.1 |
| TSP-EO #6 | 80.8 | 91.9 | 95.1 | 96.2 | 96.5 | 97.6 |
| Ethoxylated nonylphenol[3] | 95.5 | Failed (gelled) | | | | |
| Control (Low VOC Commercial Paint) | 121.1 | Failed (gelled) | | | | |

Notes:
[1]Additive loading level: 1.0 Wt % of total paint weight.
[2]Water-borne commercial paint: Weight per Gallon: 10.24 pounds per gallon; pH: 8.67; VOC: <50 g/L; Gloss at 60 degrees: 52.
[3]Nonylphenol moiety attached to 9EO Example 2 illustrates comparative examples of the present invention as against the disclosure of International Publication Number WO 2007/117512 (hereinafter sometimes referred to as the "'512 application" or "Stepan").

Example 2

The seed latex according to the '512 application (p. 20) was prepared:

Seed Latex Preparation using Sodium Lauryl Sulfate (SLS)

| Formulas: | |
|---|---|
| Water | 50 |
| Sulfate*: (29.5) | 2.44 |
| Monomers: | |
| Styrene | 7.2 |
| MMA | 12.24 |
| BA | 15.84 |
| AA | 0.72 |
| Total | 100 |
| Initiator Solution | |
| Ammonium Persulfate | 0.26 |
| Water | 14 |

Procedure: 1. Add 150 water and 7.32 g surfactant (SLS) to the kettle and heat to ~83° C. 2. Add 42.78 g initiator solution. 3. Add 108 monomer mixture to kettle and hold at ~83° C. over 2-3 hours. 4. Measure the particle size during emulsion polymerization process. 5. Cool to room temperature and keep the seed latex for future usage. The active wt % of the seed latex was 36 wt %.

Tables 5 and 6 illustrate emulsion polymerization of a styrene-acrylic latex polymer using SLS (control) and using SLS in combination with a TSP having from about 10 to 40 ethylene oxide groups as surfactant emulsifiers, respectively.

TABLE 5

Styrene-Acrylic Latex Polymer - Sodium Lauryl Sulfate (Control)

| Recipe: | Ingredient weight (g) | % BOTM |
|---|---|---|
| Kettle Charge | | |
| Deionized Water | 220.00 | |
| NaHCO3 solution | 25.00 | |
| Styrene-Acrylic Seed | 30.00 | |
| Monomer Emulsion | | |
| Deionized Water | 150.00 | |
| Sodium Lauryl Sulfate | 11.19 | 0.65 |
| TSP | 0 | 0.00 |
| Styrene | 100.00 | 20.00 |
| MMA | 170.00 | 34.00 |
| BA | 220.00 | 44.00 |
| AA | 10.00 | 2.00 |
| Initiator Solution | | |
| Deionized Water | 95.50 | |
| Ammonium Persulfate | 3.50 | 0.70 |
| NaHCO3 Solution | | |
| NaHCO3 Solution | 125.00 | |
| Total | 1160.19 | |
| Total | 1160.19 | |
| Theoretical % Solids = | | |
| Scale-up factor = | | |
| Seed = ME | 30.00 | |
| IS | 20.00 | |

TABLE 6

Styrene-Acrylic Latex Polymer - Sodium Lauryl Sulfate & TSP-EO

| Recipe: | Ingredient weight (g) | % BOTM |
|---|---|---|
| Kettle Charge | | |
| Deionized Water | 220.00 | |
| NaHCO3 solution | 25.00 | |
| Styrene-Acrylic Seed | 30.00 | |
| Monomer Emulsion | | |
| Deionized Water | 150.00 | |
| Sodium Lauryl Sulfate | 11.19 | 0.65 |
| TSP-EO | 6.5 | 1.3 |
| Styrene | 100.00 | 20.00 |
| MMA | 170.00 | 34.00 |
| BA | 220.00 | 44.00 |
| AA | 10.00 | 2.00 |
| Initiator Solution | | |
| Deionized Water | 95.50 | |
| Ammonium Persulfate | 3.50 | 0.70 |
| NaHCO3 Solution | | |
| NaHCO3 Solution | 125.00 | |
| Total | 1166.69 | |
| Total | 1166.69 | |
| Theoretical % Solids = | | |
| Scale-up factor = | | |
| Seed = ME | 30.00 | |
| IS | 20.00 | |

Procedure (For Tables 5 and 6):

1) Charge water and 25 g of NaHCO3 solution and 30 g seed latex to a kettle and heat the kettle to about 83° C. at a stirring rate of 150 rpm while purging with N2. Maintain N2 blanket throughout run. 2) Prepare monomer emulsion and initiator solution based on the recipe. 3) At ~83° C. add 20.2% Initiator solution (20.0 g) and hold for 8 minutes. 4) Feed remainder of Monomer emulsion over about 180 minutes and maintain the reaction temperature at about 83±1° C. 5) After 10 minutes of monomers additions, 79 g solution of ammonium persulfate solution with 125.0 g NaHCO₃ solution was fed for 180 minutes. 6) After addition, heat the reaction temperature to 83° C. and hold over 60 minutes at 83±1° C. 7) Cool batch to below 30° C., and adjust pH to 8.5±0.1 with concentrated (28%) ammonium hydroxide solution. 8) Filter the batch through a 100 mesh filter and store in a closed container for characterization.

TABLE 7

Resulting Properties of styrene-acrylic latex polymer using SLS (control) and using SLS in combination with a TSP as surfactant emulsifiers

| PROPERTIES: | Control - Polymer with Sodium Lauryl Sulfate (SLS) | Polymer with SLS + TSP-EO |
|---|---|---|
| % Coagulum | 0.08 | 0.21 |
| % Solids | 44.27 | 45.33 |
| % Conversion | 98.16 | 100 |
| pH (init) | 5.10 | 5.05 |
| pH (adjust) | 8.50 | 8.50 |
| Particle size (nm) | 200.7 | 200 |
| Viscosity (cps) LV3, 60 | 100 | 80 |
| F/T cycles | Yes | Yes |

Table 8-Freeze-Thaw Stability of latex binder using SLS (control) and TDA Sodium Sulfate (control), as compared to using SLS in combination with a TSP as surfactant emulsifiers and using TDA Sodium Sulfate in combination with a TSP as surfactant emulsifiers, respectively.

TABLE 8

Freeze-Thaw Stability of Latex

Viscosity (cPs, Brookfield) (LV4, 60 rpm)

| Latex Binders | Initial Vis. | 1 cycle | 2 cycles | 3 cycles | 4 cycles | 5 cycles |
|---|---|---|---|---|---|---|
| Latex Binder with SLS | 150 | 950 | 900 | 600 | 650 | 550 |
| Latex Binder with SLS/TSP-EO | 150 | 700 | 650 | 550 | 550 | 550 |
| Latex Binder with TDA sodium Sulfate | 150 | 800 | 650 | 700 | 600 | 510 |
| Latex Binder with TDA sodium Sulfate/TSP-EO | 150 | 600 | 500 | 550 | 550 | 500 |

Referring to Tables 7 and 8, the properties of the latex polymer dispersions prepared in Table 5 (Sodium Lauryl Sulfate used as the emulsifying surfactant) and Table 6 (Sodium Lauryl Sulfate and TSP used as emulsifying surfactants) both exhibit freeze thaw (F/T) stability. Using the DSC method generally known in the art, the measured Tg of the latex dispersion of Tables 5 and 6 ranged from about 24° C.-27° C.

Referring to FIG. 1, the Tg of various latex polymers prepared under the '512 application are illustrated: (1) emulsion polymerization of the latex polymer using SLS, which has a measured Tg of about 26.5° C.; (2) emulsion polymerization of the latex polymer using SLS in combination with a TSP-EO as surfactant emulsifiers, which has a measured Tg of about 25.3° C.; (3) emulsion polymerization of the latex polymer using TDA Sodium Sulfate, which has a measured Tg of about 24.5° C.; and (4) emulsion polymerization of the latex polymer using TDA Sodium Sulfate in combination with a TSP-EO as surfactant emulsifiers, which has a measured Tg of about 26.5° C.

The following Example 3 and its subsets describe the present invention as polymerizable reactive alkoxylated monomers (reactive monomers) used to form a latex comonomer or polymer.

Example 3

The following examples relate to use of tristyrylphenol (TSP) ethoxylates and tributylphenol (TBP) ethoxylates utilized as reactive monomers in preparing latex.

Example 3-1

Preparing Latex Polymers

Referring to Table 9, a control latex polymer was prepared from emulsion polymerization without the use of TSP/TBP ethoxylated monomers. Referring to Table 10, a latex polymer was prepared from emulsion polymerization using TSP ethoxylated monomers and TBP ethoxylated monomers of the present invention. The procedure for preparing the latex polymer was as follows:

Heat kettle charge to while purging with $N_2$. Maintain $N_2$ blanket throughout run. Prepare monomer emulsion and initiator solution. Add initiator solution and monomer emulsion. Hold at steady temperature and feed remainder of monomer emulsion and Initiator solution. Cool to reactor below 30° C. and then filter the batch through cheesecloth.

TABLE 9

Emulsion Polymerization without TSP/TBP ethoxylated monomer

| Recipe: | Ingredient weight (g) | % BOTM |
|---|---|---|
| Kettle Charge | | |
| Deionized Water | 320.00 | |
| Monomer Emulsion | | |
| Deionized Water | 282.00 | |
| Alkyl sulfate surfactant | 30.00 | 1.50 |
| Non-ionic surfactant | 8.00 | 0.5 |
| MMA | 320.00 | 40.00 |
| BA | 472.00 | 59.00 |
| MAA | 8.00 | 1.00 |
| Initiator Solution | | |
| Deionized Water | 156.80 | |
| Ammonium Persulfate | 3.20 | 0.40 |
| Chaser Solution | | |
| Total | 1600.00 | |
| Total | 1600.00 | |
| Theoretical % Solids = | | |
| Scale-up factor = | | |
| Seed = ME | 56.00 | |
| IS | 40.00 | |

TABLE 10

Emulsion Polymerization utilizing TSP ethoxylated monomer

| Recipe: | Ingredient weight (g) | % BOTM |
|---|---|---|
| Kettle Charge | | |
| Deionized Water | 200.00 | |
| Monomer Emulsion | | |
| Deionized Water | 176.25 | |
| Alkyl sulfate surfactant | 18.75 | 1.50 |
| Non-ionic surfactant | 5.00 | 0.50 |
| TSP-EO | 16.60 | 2.00 |
| MMA | 200.00 | 40.00 |
| BA | 295.00 | 59.00 |
| MAA | 1.68 | 1.00 |
| Initiator Solution | | |
| Deionized Water | 98.00 | |
| Ammonium Persulfate | 2.00 | 0.40 |
| Chaser Solution | | |
| Total | 1013.28 | |
| Total | 1013.28 | |
| Theoretical % Solids = | | |
| Scale-up factor = | | |
| Seed = ME | 35.66 | |
| IS | 25.00 | |

Example 3-2

Paint Formulations

Tables 11, 12 and 13 illustrate paint formulations utilizing a commercially low VOC available paint whose polymer latex is believed to have a Tg of about 2.4° C. and a $D_{50}$ of between 130-160, a similar formulation utilizing pure acrylic as the latex polymer, and a similar formulation utilizing the synthesized latexes of the present invention as the latex polymer, respectively.

Table 11—Paint Formulations

TABLE 11

Paint Formulation Control - Commercially available Low VOC paint (Comm. Paint)

| Raw materials | Pounds | Gallons | Weight Percent |
|---|---|---|---|
| Pigment Grind | | | |
| Water | 80 | 9.62 | 9.560 |
| Ethylene Glycol | 0 | 0 | 0 |
| AMP-95 | 1 | 0.13 | 0.10 |
| Rhodoline 286N | 8 | 0.91 | 0.76 |
| Antarox BL-225 | 4 | 0.48 | 0.38 |
| Rhodoline 643 | 0.5 | 0.06 | 0.05 |
| Attagel 50 | 5 | 0.253 | 0.48 |
| Titanium dioxide Tiona 595 | 230 | 7 | 22.0 |
| Water | 89.6 | 10.77 | 6.64 |
| Sub Total | 418.1 | 29.22 | |
| Letdown | | | |
| Comm. latex (undisclosed) | 480 | 54.2 | 45.9 |
| Texanol | 0 | 0 | 0 |
| Rhodoline 643 | 2.5 | 0.41 | 0.29 |
| Aquaflow NHS310 | 28 | 3.23 | 2.68 |
| Water | 95 | 11.42 | 9.1 |
| Acrysol ™ SCT-275 | 14 | 1.634 | 0.67 |
| Polyphase 663 | 4 | 0.418 | 0.38 |
| Total | 1041.6 | 100.53 | 100.0 |

TABLE 12

Paint Formulation Control - Pure Acrylic

| Raw materials | Pounds | Gallons | Weight Percent |
|---|---|---|---|
| Pigment Grind | | | |
| Water | 80 | 9.62 | 9.560 |
| Ethylene Glycol | 0 | 0 | 0.00 |
| AMP-95 | 1 | 0.13 | 0.10 |
| Rhodoline 286N | 8 | 0.91 | 0.76 |
| Antarox BL-225 | 4 | 0.48 | 0.38 |
| Rhodoline 643 | 0.5 | 0.06 | 0.05 |
| Attagel 50 | 5 | 0.253 | 0.48 |
| Titanium dioxide Tiona 595 | 230 | 7 | 22.0 |
| Water | 89.6 | 10.77 | 6.64 |
| Sub Total | 418.1 | 29.22 | |
| Letdown | | | |
| Pure Acrylic - Control | 480 | 54.2 | 45.9 |
| Texanol | 0 | 0 | 0.0 |
| Rhodoline 643 | 2.5 | 0.41 | 0.29 |
| Aquaflow NHS310 | 28 | 3.23 | 2.68 |
| Water | 95 | 11.42 | 9.1 |
| Acrysol ™ SCT-275 | 14 | 1.634 | 0.67 |
| Polyphase 663 | 4 | 0.418 | 0.38 |
| Total | 1041.6 | 100.53 | 100.0 |

Table 13—Paint Formulation with synthesized latex including TSP ethoxylate unit.

TABLE 13

Paint Formulation with synthesized latex including TSP ethoxylate unit

| Raw materials | Pounds | Gallons | Weight Percent |
|---|---|---|---|
| Pigment Grind | | | |
| Water | 80 | 9.62 | 9.560 |
| Ethylene Glycol | 0 | 0 | 0.00 |
| AMP-95 | 1 | 0.13 | 0.10 |
| Rhodoline 286N | 8 | 0.91 | 0.76 |
| Antarox BL-225 | 4 | 0.48 | 0.38 |
| Rhodoline 643 | 0.5 | 0.06 | 0.05 |
| Attagel 50 | 5 | 0.253 | 0.48 |
| Titanium dioxide Tiona 595 | 230 | 7 | 22.0 |
| Water | 89.6 | 10.77 | 6.64 |
| Sub Total | 418.1 | 29.22 | |
| Letdown | | | |
| Latex-2% - TSP/TBP reactive monomer | 480 | 54.2 | 45.9 |
| Texanol | 0 | 0 | 0.0 |
| Rhodoline 643 | 2.5 | 0.41 | 0.29 |
| Aquaflow NHS310 | 28 | 3.23 | 2.68 |
| Water | 95 | 11.42 | 9.1 |
| Acrysol ™ SCT-275 | 14 | 1.634 | 0.67 |
| Polyphase 663 | 4 | 0.418 | 0.38 |
| Total | 1041.6 | 100.53 | 100.0 |

Table 14 illustrates the resulting paint properties of the above referenced paint formulations using low Tg commercial latex, pure acrylic latex, and varying TSP/TBP ethoxylated monomers having ethoxylate groups from about 3 to 80.

TABLE 14

| | Comm. Latex | Pure Acrylic | R-TSP #1 | R-TSP #2 | R-TSP #3 | R-TSP #4 | R-TSP #5 | R-TSP #6 | R-TSP #7 | R-TBP #1 | R-TBP #2 |
|---|---|---|---|---|---|---|---|---|---|---|---|
| Viscosity: | | | | | | | | | | | |
| Initial KU | 106.8 | 103 | 101.5 | 100.3 | 97 | 84.5 | 80.1 | 95.6 | 86.6 | 98.6 | 88.4 |
| Initial, ICI | 1.2 | 1.4 | 1.6 | 1.5 | 1.6 | 1.3 | 1.4 | 1.3 | 1.4 | 1.7 | 1.4 |
| Viscosity, equilibrium | | | | | | | | | | | |
| KU | 113.4 | 106.3 | 103.8 | 103.1 | 99.4 | 88.7 | 82.3 | 93.6 | 87.1 | 101 | 93.8 |
| ICI | 1.3 | 1.4 | 1.6 | 1.6 | 1.4 | 1.2 | 1.4 | 1.4 | 1.3 | 1.6 | 1.2 |
| pH | 8.3 | 8.55 | 8.47 | 8.6 | 8.42 | 8.51 | 8.55 | 8.54 | 8.44 | 8.55 | 8.45 |
| WPG | 10.42 | 10.36 | 10.39 | 10.4 | 10.38 | 10.28 | 10.34 | 10.32 | 9.88 | 10.27 | 10.35 |
| Gloss | 20.1/ | 21.2/ | 19.2/ | 21.7/ | 20.3/ | 20.8/ | 21.3/ | 12.3/ | 2.9/ | 16.5/ | 17.0/ |

TABLE 14-continued

| | Comm. Latex | Pure Acrylic | R-TSP #1 | R-TSP #2 | R-TSP #3 | R-TSP #4 | R-TSP #5 | R-TSP #6 | R-TSP #7 | R-TBP #1 | R-TBP #2 |
|---|---|---|---|---|---|---|---|---|---|---|---|
| 20/60/85 | 57.9/ 88.4 | 60.3/ 89.4 | 56.9/ 86.4 | 60.8/ 89.6 | 59.2/ 87.3 | 59/ 87.8 | 59.9/ 88.4 | 52.6/ 81.6 | 21.5/ 40.6 | 54.5/ 87.6 | 54.8/ 87.5 |

The paint formulations utilizing Comm. Latex and Pure Acrylic latex gelled only after one F/T cycle as opposed to formulations using latexes incorporating several TSP/TBP ethoxylated monomers, which exhibited F/T stability.

Example 3-3

The properties of paint formulations using a control latex (pure acrylic), a commercially-available low Tg latex, and the TSP reactive monomers of the present invention were tested. It is observed that the resulting paint formulations wherein the above-referenced latexes varied produced comparable properties aside from F/T stability. Accordingly, the imparting of F/T stability using the reactive TSP and TBP monomer ethoxylates into latex polymers of the present invention does not detract from other desirable properties of the paint formulation (10 being the highest to 1 being the lowest).

TABLE 15

| | paint properties | | | |
|---|---|---|---|---|
| | Control - Pure Acrylic | Benchmark - Low VOC commercial paint (Comm. Latex) | R-TSP-EO #1 | R-TSP-EO #2 |
| WPG | 9.35 | 10.03 | 9.6 | 9.37 |
| pH | 8.55 | 8.3 | 8.54 | 8.49 |
| Viscosity | 77 | 109 | 94 | 77 |
| ICI | 1.00 | 1.60 | 1.05 | 1.05 |
| Gloss - @20/60/85° | 16.5/54.3/90.7 | 21.2/60.6/92.9 | 17.2/56.4/86.4 | 15.3/55.5/95.3 |
| Reflectance | 93.9 | 94 | 93.5 | 93.8 |
| Contrast Ratio | 0.972 | 0.977 | 0.972 | 0.971 |
| Low Temp. Film Formation, 40° F. | | | | |
| Sealed | 10 | 10 | 10 | 10 |
| Unsealed | 10 | 10 | 10 | 10 |
| Surfactant Leaching | | | | |
| 24 hours Dry | 8 | 7 | 7 | 8 |
| 3 Days Dry | 8 | 7 | 7 | 8 |
| 7 Days Dry | 9 | 7 | 7 | 8 |
| Foam Dab Test | 9 | 9 | 9 | 9 |
| Leveling - ASTM D4062 | 10 | 8 | 9 | 8 |
| Block Resistance, ASTM D 4946 | | | | |
| RT | 7 | 7 | 7 | 7 |
| Dry Adhesion, 7 Days | | | | |
| Aluminum | 0B | 2B | 1B | 2B |
| Alkyd | 5B | 5B | 5B | 4B |
| Open Time, minutes | | | | |
| 0 | 10 | 10 | 10 | 10 |
| 2 | 10 | 10 | 10 | 10 |
| 4 | 9 | 8 | 9 | 9 |
| 6 | 8 | 7 | 8 | 8 |
| 8 | 8 | 6 | 7 | 6 |
| 10 | 7 | 5 | 5 | 5 |
| 12 | 6 | 4 | 4 | 4 |
| 14 | 5 | 3 | 3 | 3 |
| Color Acceptance | | | | |
| E Colorant | 9 | 10 | 8 | 10 |
| B Colorant | 9 | 10 | 7 | 10 |

TABLE 16

Scrub resistance of the present invention as compared to the control (pure acrylic latex).

| Scrub Resistance | R-TSP-EO #1 | Control | R-TSP-EO #2 | Control |
|---|---|---|---|---|
| Run 1 | 838 | 1393 | 978 | 1206 |
| Run 2 | 818 | 1370 | 1086 | 1337 |

TABLE 17

Scrub resistance of the present invention as compared to a low VOC commercially-available paint formulation (Comm. Latex).

| Scrub Resistance | R-TSP-EO #1 | Comm. Paint | R-TSP-EO #2 | Comm. Paint |
|---|---|---|---|---|
| Run 1 | 736 | 2218 | 1078 | 1897 |
| Run 2 | 838 | 2115 | 943 | 1930 |

TABLE 18 stain removal properties of the present invention as compared to the control (pure acrylic latex).

| Stain Removal | R-TSP-EO #1 | Control | R-TSP-EO #2 | Control |
|---|---|---|---|---|
| Purple Crayon | 10 | 10 | 10 | 10 |
| Pencil | 10 | 10 | 10 | 10 |
| Red Lipstick | 6 | 7 | 6 | 7 |
| Ball Point Pen Black | 5 | 5 | 5 | 5 |
| Washable Marker Black | 7 | 7 | 7 | 7 |
| Sanford Highlighter Yellow | 10 | 10 | 10 | 10 |
| Gulden's Mustard | 6 | 6 | 6 | 6 |
| Coffee | 6 | 6 | 5 | 6 |
| Red Wine | 4 | 5 | 5 | 5 |

TABLE 19 stain removal properties of the present invention as compared to a low VOC commercially-available paint formulation (using low Tg Comm. Latex).

| Stain Removal | R-TSP-EO #1 | Comm. Paint | R-TSP-EO #2 | Comm. Paint |
|---|---|---|---|---|
| Purple Crayon | 10 | 10 | 10 | 10 |
| Pencil | 10 | 10 | 10 | 10 |
| Red Lipstick | 6 | 7 | 7 | 7 |
| Ball Point Pen Black | 4 | 5 | 5 | 6 |
| Washable Marker Black | 7 | 7 | 7 | 7 |
| Sanford Highlighter Yellow | 10 | 10 | 10 | 10 |
| Gulden's Mustard | 5 | 5 | 5 | 5 |
| Coffee | 6 | 6 | 6 | 6 |
| Red Wine | 4 | 4 | 4 | 4 |

The following Example 4 and its subsets describe the present invention as surface active alkoxylated compounds utilized as one or more additives to an aqueous dispersion of latex polymer or copolymer.

Example 4

Surface active alkoxylated compounds as additives.

Non-ionic TSP surfactants having ethylene oxide groups greater than about 3 to about 80 was added at 10 lbs/100 gals in Pure acrylic-White base, and the formulation exhibited freeze-thaw stability.

Table 20 shows anionic TSP surfactants of the present invention (10 bs/100 gals) as FfT additives (in Pure acrylic-White base).

TABLE 20

Freeze-Thaw Stability of Low VOC Paints

| Commercial Semigloss Paint with varying amounts of (anionic) F/T additive | Stormer Viscosity (Krebs Unit, KU) | | | | | |
|---|---|---|---|---|---|---|
| | Initial Vis. | 1 cycle | 2 cycles | 3 cycles | 4 cycles | 5 cycles |
| TSP-EO phosphate ester salt | 82.9 | 86.6 | 88.8 | 89.4 | 90.4 | 91.5 |
| Low nonionic TSP-EO phosphate ester salt | 77.8 | 85.6 | 87.4 | 88.0 | 89.6 | 91.2 |
| TSP-EO TEA salt | 81.7 | 91.0 | 93.5 | 94.0 | 95.5 | 97.9 |
| TSP-EO Ammonium Sulfate Salt | 78.0 | 88.3 | 90.2 | 91.6 | 93.3 | 101.4 |
| TSP-EO Potassium Salt 1 | 76.6 | 84.8 | 85.1 | 86.2 | 85.9 | 86.7 |
| TSP-EO Potassium Salt 2 | 81.3 | 90.7 | 92.6 | 93.8 | 93.3 | 94.7 |
| TSP-EO-PO | 81.3 | 92.6 | 95.3 | 97.8 | 102.2 | 104.9 |

Example 4-1

Table 21 shows the effects of the TSP ethoxylate of the present invention on the binder particle size. The mean particle size was measured using a Zetasizer Nano ZS device utilizing the Dynamic Light Scattering (DLS) method. The DLS method essentially consists of observing the scattering of laser light from particles, determining the diffusion speed and deriving the size from this scattering of laser light, using the Stokes-Einstein relationship.

TABLE 21

Effects of TSP Ethoxylate on Particle sizes of Low Tg Binder

| TSP | Low VOC Comm. Paint (3.0 wt %) | Mean Particle Size (nm) | | | | | |
|---|---|---|---|---|---|---|---|
| | | Initial Vis. | 1 cycle | 2 cycles | 3 cycles | 4 cycles | 5 cycles |
| TSP-EO A | 220.75 + 6.62 | 142.8 | 137.5 | 149.9 | 154.3 | 158.8 | 145.4 |
| TSP-EO B | 220.75 + 8.28 | 146.9 | 161.1 | 158.3 | 169.7 | 164.2 | 189.0 |

Example 4-2

Table 22 shows the loading level of TSP Ethoxylate of the present invention on FIT Stability of low VOC Paints.

TABLE 22

Loading Level of TSP-EO on Freeze-Thaw Stability of Low VOC Semigloss Paints

| TSP-EO (wt % based on dry polymer weight) | Viscosity (Krebs Units, KU) | | | | | |
|---|---|---|---|---|---|---|
| | Initial Vis. | 1 cycle | 2 cycles | 3 cycles | 4 cycles | 5 cycles |
| 0 | 115.4 | Gel | — | — | — | — |
| 0.86 | 114.6 | 126.3 | gel | — | — | — |
| 1.30 | 101.4 | 128.7 | >140 | gel | — | — |
| 1.71 | 110.5 | 109 | 113.6 | 120.2 | 129.3 | gel |
| 2.57 | 106.6 | 102.3 | 103.8 | 103.8 | 106.9 | 109.2 |
| 3.43 | 105.1 | 102.3 | 102.6 | 102.6 | 103.8 | 105.8 |
| 4.29 | 104.1 | 100.9 | 101.4 | 101.2 | 102.3 | 104.1 |
| 8.00 | 93.2 | 97.5 | 98.5 | 98.8 | 100.3 | 101.2 |

Referring to Table 23, F/T stability is observed at or above about 1.3% based on the total polymer weight using the TSP-EO of the present invention.

TABLE 23

Loading Level of TSP-EO on Freeze-Thaw Stability of Low VOC Flat Paints

| TSP-EO (wt % based on dry polymer weight) | Viscosity (Krebs Units, KU) | | | | | |
|---|---|---|---|---|---|---|
| | Initial Vis. | 1 cycle | 2 cycles | 3 cycles | 4 cycles | 5 cycles |
| 280.5 + 0.00 | 104.8 | gel | — | — | — | — |
| 280.5 + 0.56 | 102.4 | 108.6 | 116.6 | 122 | 131.4 | 136 |
| 280.5 + 1.11 | 100.4 | 104.2 | 108.5 | 111.8 | 117.5 | 120.5 |
| 280.5 + 1.67 | 98.5 | 100.1 | 102.4 | 104 | 106.7 | 109.6 |
| 280.5 + 2.22 | 96 | 97.2 | 98.5 | 99.7 | 102 | 104.2 |
| 280.5 + 2.78 | 95.5 | 95.4 | 96.4 | 97.3 | 99.2 | 100.3 |

Example 4-3

TSP ethoxylates in varying amounts were added to low or zero VOC commercial paints and tested for freeze thaw stability. Table 24 shows the effects of TSP-EO of the present invention on F/T Stability of various Low/Zero VOC Commercial Paints. The control contained no TSP ethoxylated surfactant (TSP-EO).

TABLE 24

| Low/Zero VOC Commercial Paints | Starting Viscosity | | | Freeze-Thaw Stability Viscosity, (KU) after 1, 2, 3, 4, and 5 cycles | | |
|---|---|---|---|---|---|---|
| | Control | 10.0 lbs/100 gals | 15.0 lbs/100 gals | Control | 10.0 lbs/100 gals of added F/T additive | 15.0 lbs/100 gals of added F/T additive |
| Paint 1 (advertised as 0 VOC) | 112.1 | 91.2 | 88.3 | 130/>140/140.0/139.4/139.2 | 101.9/116.2/123.1/102.2/102.6 | 88.3/98.3/121.8/103.8/100.7 |
| Paint 2 (advertised as 37 g/L) | 109.2 | 98.5 | 95 | gel/— | 105.2/106.5/102.9/100.9/100.0 | 95.6/95.7/93.8/94.3/94.4 |
| Paint 3 (advertised as 0 VOC) | 102.3 | 80.8 | 73.8 | gel/— | 91/107.8/108.0/108.6/111.4 | 85.9/99.8/99.9/99.2/100.0 |
| Paint 4 (advertised as Low VOC) | 99.9 | 97.6 | 101.1 | gel/— | 123.8/gel/— | 126.4/gel/— |
| Paint 5 (advertised as 41 g/L) | 108.4 | 86.6 | 80.8 | gel/— | 120.1/gel/— | 106.9/89.4/115.2/117.1/118.2 |
| Paint 6 (advertised as 0 VOC) | 111.5 | 93.7 | 87.2 | gel/— | gel/— | 98.6/107.6/99.4/100.4/99.5 |
| Paint 7 (advertised as 0 VOC) | 105.5 | 87 | 85 | gel/— | 96.5/114.5/107.7/106.9/107.3 | 92.4/109.4/103.8/106.2/104.9 |
| Paint 8 (advertised as 0 VOC) | 102.7 | 84 | 79.3 | 121.1/gel/— | 86.3/97.7/97.1/91.3/92.2 | 82.8/96.1/85.9/88.0/88.4 |
| Paint 9 (advertised as 50 g/L) | 119.4 | 89.8 | 87.6 | gel/— | 126.2/gel/— | 127.1/gel/— |
| Paint 10 (advertised as 50 g/L) | 112.5 | 88.7 | 83.2 | gel/— | 93.7/93.7/92.0/94.1/91.0 | 87.8/93.5/86.3/86.6/86.7 |
| Paint 11 (advertised as 50 g/L) | 107.2 | 91 | 84.8 | gel/— | gel/— | 102.2/98.4/95.0/95.6/94.5 |
| Paint 12 (advertised as 50 g/L) | 120.6 | 95.1 | 84.3 | gel/— | 114.3/gel/— | 94.4/109.4/102.0/102.5/102.5 |

Example 4-5

Open time-Tables 25 and 26 show the effects of TSP Ethoxylate nonionic surfactants on "open time" of Low VOC Paints and the Effects of TSP Ethoxylate Anionic Surfactants on "open time" of Low VOC Paints, respectively. Open time is generally understood to be the interval, after the paint is applied, during which it can be blended with additional painted regions (at the "wet edge"). Open time refers to the amount of time a newly-applied layer of paint remains workable before brush strokes and other signs of manipulation become visible in dried films. The method for measuring Open Time is generally as follows: a 10 mils film is drawn down on a piece of black scrub test paper. The paint film is then cross-hatched in two-inch intervals with the eraser end of a pencil. The first cross hatch then brushed over in one direction 15 times; this is then repeated in two-minute intervals for each successive cross-hatch. After 48 hrs, the dry films are examined for the earliest times at which traces of cross-hatch at discernable. This is performed under constant humidity, room temp. It is desirable for paint formulations to have an open time of greater than 4 minutes, typically, greater than 6 minutes. The amount of reagent (both nonionic surfactants and anionic surfactants) varied from about 2.5 grams surfactant to about 4.25 grams surfactant per 256 grams of paint.

TABLE 25

| Reagent (Nonionic Surfactants) | starting viscosity (KU) | open time (minutes) sample | Control |
|---|---|---|---|
| TSP-EO #1 | 89.9 | >14 | 4 |
| TSP-EO #2 | 85 | >14 | 4 |
| TSP-EO #3 | 82 | 14 | 2 to 4 |
| TSP-EO #4 | 81.2 | >14 | 4 |
| TSP-EO #5 | 89.9 | 4 | 2 |

TABLE 26

| Reagent (Anionic Surfactants) | starting viscosity (KU) | open time (minutes) sample | Control |
|---|---|---|---|
| TSP-EO TEA salt | 83.3 | 14 | 2 to 4 |
| TSP-EO Ammonium Sulfate Salt | 83.5 | 8 to 10 | 2 |
| TSP-EO Potassium Salt 1 | 86.4 | 8 to 12 | 2 |
| TSP-EO-PO | 83.5 | >14 | 4 |

Referring back to Tables 25 and 26, it is observed that open time increased significantly when utilizing either the nonionic TSP additives or anionic TSP additives, respectively.

In the above detailed description, preferred embodiments are described in detail to enable practice of the invention. Although the invention is described with reference to these specific preferred embodiments, it will be understood that the invention is not limited to these preferred embodiments. But to the contrary, the invention includes numerous alternatives, modifications and equivalents as will become apparent from consideration of the following detailed description. It is understood that upon reading the above description of the present invention, one skilled in the art could make changes and variations therefrom. These changes and variations are included in the spirit and scope of the following appended claims.

What is claimed is:

1. A latex polymer binder derivable from:
   at least one first monomer, and
   at least one second monomer of formula:

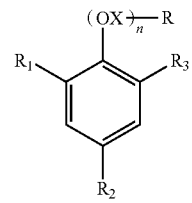

wherein:
   $R_1$, $R_2$, and $R_3$ are independently selected from the group consisting of:

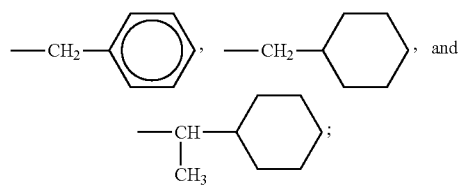

X comprises a divalent hydrocarbon radical comprising a linear or branched alkylene radical having from about 2 to 8 carbon atoms;
   n is an integer ranging from 1 to 100; and
   R comprises at least one acrylate, $C_1$-$C_6$ alkyl acrylate, allyl, vinyl, maleate, itaconate, fumarate, acrylo, methacrylo, acrylamido, methacrylamido, diallylamino, allyl ether, vinyl ether, α-alkenyl, maleimido, styrenyl, or α-alkyl styrenyl group; and
   further wherein said latex polymer binder is a binder having a glass transition temperature (Tg) ranging from about −5° C. to about 5° C.

2. The binder of claim 1, wherein R comprises at least one acrylate, $C_1$-$C_6$ alkyl acrylate, allyl, vinyl, maleate, itaconate or fumarate.

3. The binder of claim 1, wherein R comprises at least one acrylo, methacrylo, acrylamido, methacrylamido, diallylamino, allyl ether, vinyl ether, α-alkenyl, maleimido, styrenyl, or α-alkyl styrenyl group.

4. The binder of claim 1, wherein R comprises:
   $R^a$CH═C($R^b$)COO—,
   wherein $R^a$ is H, and $R^b$ comprises H or a $C_1$-$C_4$ alkyl.

5. The binder of claim 1, wherein R comprises
   —HC═CYZ or —OCH═CYZ,
   wherein:
   Y is H, $CH_3$, or Cl;
   Z is CN, Cl, —COOR$^c$, —$C_6H_4R^c$, —COOR$^d$, or —HC═$CH_2$;
   $R^d$ is $C_1$-$C_8$ alkyl or $C_2$-$C_8$ hydroxy alkyl; and
   $R^c$ is H, Cl, Br, or $C_1$-$C_4$ alkyl.

6. The binder of claim 1, wherein n is an integer ranging from about 10 to about 50.

7. The binder of claim 6, wherein n is an integer ranging from about 20 to about 50.

8. The binder of claim 1, wherein the first monomer comprises at least one acrylic monomer comprising acrylic acid, acrylic acid ester, methacrylic acid, methacrylic acid ester, or a mixture thereof.

9. The binder of claim 8, wherein the binder is further derivable from at least one third monomer comprising styrene, alpha-methyl styrene, vinyl chloride, acrylonitrile, methacrylonitrile, ureido methacrylate, vinyl acetate, a vinyl ester of a branched tertiary monocarboxylic acid, itaconic acid, crotonic acid, maleic acid, fumaric acid, ethylene, or a $C_4$-$C_8$ conjugated diene.

10. The binder of claim 1, wherein the binder has a glass transition temperature (Tg) ranging from about −5° C. to about 0° C.

11. The binder of claim 1, wherein the binder has a mean particle size of less than about 200 nm.

12. The binder of claim 1, wherein the binder has a mean particle size of less than about 190 nm.

13. The binder of claim 1, wherein the binder has a mean particle size of less than about 175 nm.

14. A method for imparting freeze-thaw stability to a low VOC coating composition, comprising:

forming the composition with a latex polymer binder prepared by copolymerizing:

(1) at least one first monomer with
(2) at least one second monomer of formula:

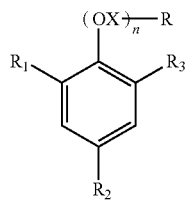

wherein:

$R_1$, $R_2$, and $R_3$ are independently selected from the group consisting of:

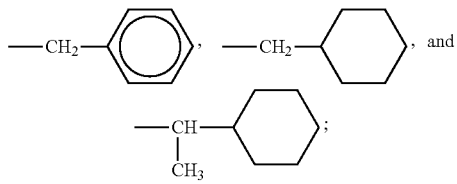

X comprises a divalent hydrocarbon radical comprising a linear or branched alkylene radical having from about 2 to 8 carbon atoms;

n is an integer ranging from 1 to 100; and

R comprises at least one acrylate, $C_1$-$C_6$, alkyl acrylate, allyl, vinyl, maleate, itaconate, fumarate, acrylo, methacrylo, acrylamido, methacrylamido, diallylamino, allyl ether, vinyl ether, α-alkenyl, maleimido, styrenyl, or α-alkyl styrenyl group; and further wherein the binder has a glass transition temperature (Tg) ranging from about −5° C. to about 5° C., and freeze-thaw stability is imparted to the low VOC coating composition.

15. The method of claim 14, wherein the binder has a glass transition temperature (Tg) ranging from about −5° C. to about 0° C.

16. The method of claim 15, wherein the binder has a mean particle size of less than about 200 nm.

17. The method of claim 14, wherein the binder has a mean particle size of less than about 190 nm.

18. The method of claim 14, wherein the binder has a mean particle size of less than about 175 nm.

* * * * *